US011096923B2

(12) United States Patent
Dunman et al.

(10) Patent No.: US 11,096,923 B2
(45) Date of Patent: Aug. 24, 2021

(54) PHARMACEUTICAL COMPOSITION CONTAINING POLYMYXIN B/TRIMETHOPRIM BASED THERAPEUTICS

(71) Applicant: University of Rochester, Rochester, NY (US)

(72) Inventors: Paul M. Dunman, Pittsford, NY (US); Rachel Wozniak, Pittsford, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 16/325,752

(22) PCT Filed: Aug. 16, 2017

(86) PCT No.: PCT/US2017/047060
§ 371 (c)(1),
(2) Date: Feb. 15, 2019

(87) PCT Pub. No.: WO2018/035183
PCT Pub. Date: Feb. 22, 2018

(65) Prior Publication Data
US 2019/0175550 A1 Jun. 13, 2019

Related U.S. Application Data

(60) Provisional application No. 62/489,535, filed on Apr. 25, 2017, provisional application No. 62/375,720, filed on Aug. 16, 2016.

(51) Int. Cl.
| *A61K 31/395* | (2006.01) |
| *A61K 31/505* | (2006.01) |
| *A61K 31/496* | (2006.01) |
| *A61P 31/04* | (2006.01) |
| *A61P 27/02* | (2006.01) |
| *A61P 27/06* | (2006.01) |
| *A61P 27/12* | (2006.01) |
| *A61K 31/7036* | (2006.01) |

(52) U.S. Cl.
CPC .......... *A61K 31/395* (2013.01); *A61K 31/496* (2013.01); *A61K 31/505* (2013.01); *A61K 31/7036* (2013.01); *A61P 27/02* (2018.01); *A61P 27/06* (2018.01); *A61P 27/12* (2018.01); *A61P 31/04* (2018.01)

(58) Field of Classification Search
CPC .. A61K 31/395; A61K 31/496; A61K 31/505; A61P 27/02; A61P 27/06; A61P 27/12; A61P 31/04
See application file for complete search history.

(56) References Cited

U.S. PATENT DOCUMENTS

| 3,852,450 A | * | 12/1974 | Silvestri | ............ | A61K 2300/00 514/272 |
| 3,985,873 A | * | 10/1976 | Alvan | ................ | A61K 9/0048 514/2.4 |
| 4,152,444 A | * | 5/1979 | Vischer | ................ | A61K 31/495 514/183 |
| 5,104,875 A | * | 4/1992 | Jurgen | ................ | A61K 31/495 514/252.13 |
| 2010/0105662 A1 | * | 4/2010 | Tyle | ....................... | A61K 31/55 514/217.07 |

FOREIGN PATENT DOCUMENTS

| CN | 105492004 | | 4/2016 |
| EP | 0592348 | | 4/1994 |
| GB | 1484329 | | 9/1977 |
| GB | WO2014/188178 | * | 11/2014 |
| JP | 1975095418 A | | 7/1975 |
| JP | 1994239762 A | | 8/1994 |
| WO | 2010051291 | | 5/2010 |
| WO | 2016013986 A1 | | 1/2016 |

OTHER PUBLICATIONS

Noziketal. in Annals of Ophthalmology 17(12)746-748 (1985) (Year: 1985).*
Polytrim at https://web.archive.org/web/20160319103733/ http://www.odspecs.com/meddetails/polytrim.html (Year: 2016).*
Polytrim Label at https://dailymed.nlm.nih.gov/dailymed/fda/fdaDrugXsl.cfm?setid=5ce95658-d2eb-4d35-b387-ded0d7e4a122&type=display (Year: 2019).*
Goodman and Gilman's The Pharmacological Basis of Therapeutics, Tenth Edition (2001), McGraw Hill, Chapter I, pp. 3-29 (Year: 2001).*
Orden Martinez et al. in Anales de Pediatria, 61(1), 32-36 (2004) (Year: 2004).*
Orden Martinez et al. in Anales de Pediatria, 61(1), 32-36 (2004) (Machine Translation) (Year: 2004).*
Yoon et al. in Antimicrobial Agents and Chemotherapy, 753-757 (2004) (Year: 2004).*
Eleman et al. in Journal of Clinical Microbiology 3558-3562 (2010) (Year: 2010).*
Rosenblatt et al. in Antimicrobial Agents and Chemotherapy, 84-92 (1974) (Year: 1974).*
Chojnacki et al. in Antimicrobial Agents Chemotherapy, 2019, 63(10) e00777-19 (Year: 2019).*
Chojnacki et al. in Antimicrobial Agents Chemotherapy, 2019, 63(1) e01929-18 (Year: 2019).*
Allewelt M, Coleman FT, Grout M, Priebe GP, Pier GB. Acquisition of expression of the Pseudomonas aeruginosa ExoU cytotoxin leads to increased bacterial virulence in a murine model of acute pneumonia and systemic spread. Infection and immunity 2000;68:3998-4004.

(Continued)

*Primary Examiner* — Dennis Heyer
(74) *Attorney, Agent, or Firm* — Riverside Law LLP

(57) ABSTRACT

The present invention features an antibacterial composition comprising 1) a composition A comprising polymyxin B and trimethoprim; and 2) an antibiotic agent selected from the group consisting of rifampicin, rifabutin, rifapentine, rifaximin, pefloxacin mesylate, sparfloxacin, sarafloxacin HCl, tobramycin, lomefloxacin, besifloxacin, danofloxacin mesylate, enrofloxacin, nadifloxacin and clinafloxacin, a topical pharmaceutical thereof, and a method of treating bacterial infections using mixtures of 1 and 2.

28 Claims, 8 Drawing Sheets
Specification includes a Sequence Listing.

(56) References Cited

OTHER PUBLICATIONS

Bertino JS. Impact of antibiotic resistance in the management of ocular infections: the role of current and future antibiotics. Clinical ophthalmology (Auckland, NZ) 2009;3:507-521.
Blanchard C, Brooks L, Ebsworth-Mojica K, et al. Zinc Pyrithione Improves the Antibacterial Activity of Silver Sulfadiazine Ointment. mSphere 2016;1:e00194-16, 14 pages.
Chang VS, Dhaliwal DK, Raju L, Kowalski RP. 2015. Antibiotic Resistance in the Treatment of Staphylococcus aureus Keratitis: a 20-Year Review. Cornea 34:698-703 (doi: 10.1097/ICO.0000000000000431), 6 pages.
Collier SA, Gronostaj MP, MacGurn AK, et al. Estimated burden of keratitis—United States, 2010. MMWR Morbidity and mortality weekly report 2014;63: 1027-1030.
Colquhoun JM, Wozniak RA, Dunman PM. Clinically Relevant Growth Conditions Alter Acinetobacter baumannii Antibiotic Susceptibility and Promote Identification of Novel Antibacterial Agents. PloS one 2015;10:e0143033, 14 pages.
Fischbach MA. Combination therapies for combating antimicrobial resistance. Current opinion in microbiology 2011; 14:519-523.
George A Pankey et al, "Detection of synergy using the combination of polymyxin B with either meropenem or rifampin against carbapenemase-producing", Diagnostic Microbiology and Infectious Disease, Elsevier, Amsterdam, NL, vol. 70, No. 4, doi:10.1016/J.DISGMICROBIO.2011.05.003, ISSN 0732-8893, (May 4, 2011), pp. 561-564, (May 11, 2011), XP028266800.
Gillaspy AF, Hickmon SG, Skinner RA, Thomas JR, Nelson CL, Smeltzer MS. Role of the accessory gene regulator (agr) in pathogenesis of staphylococcal osteomyelitis. Infection and immunity 1995;63:3373-3380.
Granet DB, Dorfman M, Stroman D, Cockrum P. 2008. A multicenter comparison of polymyxin B sulfate/trimethoprim ophthalmic solution and moxifloxacin in the speed of clinical efficacy for the treatment of bacterial conjunctivitis. Journal of pediatric ophthalmology and strabismus 45:340-349 (DOI: 10.3928/01913913-20081101-07).
Green M, Apel A, Stapleton F. 2008. Risk factors and causative organisms in microbial keratitis. Cornea 27:22-27 (doi: 10.1097/ICO.0b013e318156caf2).
International Search Report, PCT/US2017/047060, dated Nov. 15, 2017, 5 pages.
J.W. Betts et al, "Rifaximin combined with polymyxins: A potential regimen for selective decontamination of multidrug-resistant bacteria in the digestive tract?", Journal of Global Antimicrobial Resistance, (Mar. 1, 2016), vol. 4, doi:10.1016/j.jgar.2015.11.008, ISSN 2213-7165, pp. 11-15, XP055419906.
Jacobs AC, Blanchard CE, Catherman SC, Dunman PM, Murata Y. An ribonuclease T2 family protein modulates Acinetobacter baumannii abiotic surface colonization. PloS one 2014;9:e85729 (doi:10.1371/journal.pone.0085729), 10 pages.
Ledbetter EC, Mun JJ, Kowbel D, Fleiszig SM. Pathogenic phenotype and genotype of Pseudomonas aeruginosa isolates from spontaneous canine ocular infections. Investigative ophthalmology & visual science 2009;50:729-736.
Lichtenstein SJ, Wagner RS, Jamison T, Bell B, Stroman DW., 2007, Speed of bacterial kill with a fluoroquinolone compared with nonfluoroquinolones: clinical implications and a review of kinetics of kill studies. Advances in therapy 24:1098-1111 (DOI: 10.1007/bf02877716).
Lomholt JA, Poulsen K, Kilian M. Epidemic population structure of Pseudomonas aeruginosa: evidence for a clone that is pathogenic to the eye and that has a distinct combination of virulence factors. Infection and immunity 2001;69:6284-6295.
Lotti R, Dart JK. 1992. Cataract as a complication of severe microbial keratitis. Eye (London, England) 6 ( Pt 4):400-403 (DOI: 10.1038/eye.1992.82).
Nozik RA, Smolin G, Knowlton G, Austin R. 1985. Trimethoprim-polymyxin B ophthalmic solution in treatment of surface ocular bacterial infections. Annals of ophthalmology 17:746-748.

Price FW, Jr., Dobbins K, Zeh W. 2002. Penetration of topically administered ofloxacin and trimethoprim into aqueous humor. Journal of ocular pharmacology and therapeutics: the official journal of the Association for Ocular Pharmacology and Therapeutics 18:445-453 (DOI: 10.1089/10807680260362722).
R Wagner, "Results of a survey of children with acute bacterial conjunctivitis treated with trimethoprim-polymyxin B ophthalmic solution", Clinical Therapeutics., US, (Oct. 1, 1995), vol. 17, No. 5, doi:10.1016/0149-2918(95)80065-4, ISSN 0149-2918, pp. 875-881, XP055419603.
Resnikoff S, Pascolini D, Etya'ale D, Kocur I, Pararajasegaram R, Pokharel GP, Mariotti SP. 2004. Global data on visual impairment in the year 2002. Bulletin of the World Health Organization 82:844-851.
Rhee M K et al, "A laboratory evaluation of antibiotic therapy for ciprofloxacin-resistant pseudomonas aeruginosa", American Journal of Ophthalmo, Elsevier, Amsterdam, NL, (Aug. 1, 2004), vol. 138, No. 2, doi:10.1016/J.AJO.2004.03.016, ISSN 0002-9394, pp. 226-230, XP004723184.
Stepinska et al., Diverse type III secretion phenotypes among Pseudomonas aeruginosa strains upon infection of murine macrophage-like and endothelial cell lines. Microbial pathogenesis, 2008, 44: 448-458.
Van Rensburg SF, Gibson JR, Harvey SG, Burke CA. 1982. Trimethoprim-polymyxin ophthalmic solution versus chloramphenicol ophthalmic solution in the treatment of bacterial conjunctivitis. Pharmatherapeutica 3:274-277.
Whitcher JP, Srinivasan M, Upadhyay MP. 2001. Corneal blindness: a global perspective. Bulletin of the World Health Organization 79:214-221.
Worthington RJ, Melander C. Combination approaches to combat multidrug-resistant bacteria. Trends in Biotechnology 2013; 31:177-184.
Written Opinion, PCT/US2017/047060, dated Nov. 15, 2017, 6 pages.
Zarei-Ghanavati S, Baghdasaryan E, Ramirez-Miranda A, Nguyen M, Yu F, Lee GJ, Deng SX. 2011. Elevated intraocular pressure is a common complication during active microbial keratitis. American journal of ophthalmology 152:575-581 e571 (doi: 10.1016/j.ajo.2011.03.014).
Bollenbach, "Antimicrobial interactions: mechanisms and implications for drug discovery and resistance evolution," Current Opinion in Microbiology, 2015, 27:1-9.
Brochado et al., "Species-specific activity of antibacterial drug combinations," Nature, 2018, 559:259-263.
Gunnison et al., 1953. Studies on Antibiotic Synergism and Antagonism: The Effect in Vitro of Combinations of Antibiotics on Bacteria of Varying Resistance to Single Antibiotics. J Bacteriol. Aug;66(2):150-8.
Jawetz et al.,1952, Studies on Antibiotic Synergism and Antagonism: Synergism among Seven Antibiotics against Various Bacteria in vitro. J Bacteriol. Jul; 64(1): 29-39.
Manten and De Nooy, 1956, The Activity of Some Antibiotic Combinations on Salmonella. Antonie van Leeuwenhoek vol. 22, pp. 231-236.
Alexandrakis, G., E.C. Alfonso, and D. Miller, Shifting trends in bacterial keratitis in south Florida and emerging resistance to fluoroquinolones. Ophthalmology, 2000. 107(8): p. 1497-502.
American Academy of Ophthlamology Preferred Practice Guidelines: Bacterial Keratitis. San Francisco, CA: American Academy of Ophthalmology, 2018, 55 pages.
Antibiotic Resistance Threats in the United States. 2019, U.S. Department of Health and Human Services, CDC: Atlanta, GA, 150 pages.
Antimicrobial Resistance: Tackling a Crisis for the Health and Wealth of Nations, in Review on Antimicrobial Resistance. 2014, Wellcome Trust, 20 pages.
Asbell, P.A., et al., Antibiotic Resistance Among Ocular Pathogens in the United States: Five-Year Results From the Antibiotic Resistance Monitoring in Ocular Microorganisms (ARMOR) Surveillance Study. JAMA ophthalmology, 2015. 133(12) 10 pages.

(56) References Cited

OTHER PUBLICATIONS

Chojnacki, M., et al., A Novel, Broad-Spectrum Antimicrobial Combination for the Treatment of Pseudomonas aeruginosa Corneal Infections. Antimicrob Agents Chemother, 2019. 63(10) 4 pages.

Chojnacki, M., et al., Development of a Broad-Spectrum Antimicrobial Combination for the Treatment of *Staphylococcus aureus* and Pseudomonas aeruginosa Corneal Infections. Antimicrob Agents Chemother, 2019. 63(1) 13 pages.

Folks et al., 1988, "Clinical Comparison of Topical Solutions Containing Trimethoprim in Treating Ocular Surface Bacterial Infections." J Ocul Pharmacol, 4(2): 111-115.

Lamberts et al. 1984, "Clinical Evaluation of Trimethoprim-containing Ophthalmic Solutions in Humans." American Journal of Ophthalmology, 98(1): 11-16.

Laskey, E., et al., Efficacy of a Novel Ophthalmic Antimicrobial Drug Combination Toward a Large Panel of *Staphylococcus aureus* Clinical Ocular Isolates From Around the World. Cornea, 2020. 39(10): p. 1278-1284.

Ni, N., et al., Seasonal, geographic, and antimicrobial resistance patterns in microbial keratitis: 4-year experience in eastern Pennsylvania. Cornea, 2015. 34(3) 7 pages.

Plackett, B., Why big pharma has abandoned antibiotics. Nature, 2020. 586(7830): p. S50-s52.

Rice, L.B., Federal funding for the study of antimicrobial resistance in nosocomial pathogens: no ESKAPE. J Infect Dis, 2008. 197(8): p. 1079-81.

Polytrim, [Online], May 19, 2016, Obtained a file recorded on May 19, 2016, http://web.archive.org/[researched on Mar. 2, 2021], internet, <URL:https://web.archive.org/web/20160319103733/http://www.odspecs.com/meddetails/polytrim.html>.

Perloth et al., "Adjunctive Use of Rifampin for the Treatment of *Staphylococus aureus*Infections." Arch Intern Med, 2008, 168(8): 805-819.

\* cited by examiner

PHARMACEUTICAL COMPOSITION CONTAINING POLYMYXIN B/TRIMETHOPRIM BASED THERAPEUTICS

CROSS REFERENCE TO RELATED APPLICATIONS

This application is a U.S. national phase application filed under 35 U.S.C. § 371 claiming benefit to International Patent Application No. PCT/US2017/047060, filed Aug. 16, 2017, which is entitled to priority under 35 U.S.C. § 119(e) to U.S. Provisional Patent Application No. 62/375,720, filed Aug. 16, 2016, and U.S. Provisional Patent Application No. 62/489,535, filed Apr. 25, 2017, each of which application is hereby incorporated herein by reference in its entirety.

STATEMENT REGARDING FEDERALLY SPONSORED RESEARCH OR DEVELOPMENT

This invention was made with government support under 1R01AI103507 awarded by the National Institutes of Health. The government has certain rights in the invention.

FIELD

The present invention relates to an anti-bacterial composition for the treatment of bacterial infection, particularly bacterial infection in an ocular tissue such as bacterial keratitis.

BACKGROUND OF THE INVENTION

Ophthalmic or ocular disorders/diseases have historically been recognized as complex and vision threatening. Although numerous pharmaceutical agents and compositions exist for their treatments, their side effects profile and effectiveness are less than desired. Bacterial corneal infection (keratitis) is a potentially devastating ophthalmic disease. Acute infections can present with dense corneal infiltrates with subsequent ulceration and perforation which, despite aggressive treatment, can result in long term, vision-threatening sequelae such as corneal scarring, glaucoma and cataract. See Lotti R, Dart J K. 1992. Cataract as a complication of severe microbial keratitis. Eye (London, England) 6 (Pt 4):400-403; and Zarei-Ghanavati S, Baghdasaryan E, Ramirez-Miranda A, Nguyen M, Yu F, Lee G J, Deng S X. 2011. Elevated intraocular pressure is a common complication during active microbial keratitis. American journal of ophthalmology 152:575-581 e571. In fact, worldwide, corneal opacification due to ulceration is a leading cause of vision loss contributing approximately 2 million new cases of blindness each year. See Resnikoff S, Pascolini D, Etya'ale D, Kocur I, Pararajasegaram R, Pokharel G P, Mariotti S P. 2004. Global data on visual impairment in the year 2002. Bulletin of the World Health Organization 82:844-851; and Whitcher J P, Srinivasan M, Upadhyay M P. 2001. Corneal blindness: a global perspective. Bulletin of the World Health Organization 79:214-221.

As bacterial keratitis can present with rapid progression resulting in permanent visual loss in a matter of hours, immediate broad coverage empiric treatment is necessary. Two of the most frequent causative organisms are *Staphylococcus aureus* and *Pseudomonas aeruginosa*, thus a topical fluoroquinolone, particularly fourth-generation agents such as moxifloxacin or gatifloxacin, are commonly used for broad spectrum activity against Gram-positive and –negative organisms. See Green M, Apel A, Stapleton F. 2008. Risk factors and causative organisms in microbial keratitis. Cornea 27:22-27. However, rates of fluoroquinolone resistance are on the rise. Indeed, antimicrobial susceptibility testing of MRSA keratitis isolates collected between 1993 and 2012 found that approximately 35.2% and 45.9% of isolates tested displayed resistance to moxifoxacin and gatifloxacin, respectively. See Chang V S, Dhaliwal D K, Raju L, Kowalski R P. 2015. Antibiotic Resistance in the Treatment of *Staphylococcus aureus* Keratitis: a 20-Year Review. Cornea 34:698-703. That same study found that resistance rates to sulfamethoxazole (5.7% resistance) and trimethoprim (11.5% resistance) are among the lowest of all antibiotics evaluated, suggesting that agents containing either of these agents would be more efficacious toward MRSA than fourth-generation fluoroquinolones. Thus, it may not be surprising that trimethoprim in combination with polymixin B (Polytrim) is a common topical agent for ocular infections. See Nozik R A, Smolin G, Knowlton G, Austin R. 1985. Trimethoprim-polymyxin B ophthalmic solution in treatment of surface ocular bacterial infections. Annals of ophthalmology 17:746-748; and van Rensburg S F, Gibson J R, Harvey S G, Burke C A. 1982. Trimethoprim-polymyxin ophthalmic solution versus chloramphenicol ophthalmic solution in the treatment of bacterial conjunctivitis. Pharmatherapeutica 3:274-277. However, Polytrim is slow acting, displays limited ocular tissue penetration, and demonstrates limited potency in comparison to other ophthalmic antimicrobial agents. See Speed of bacterial kill with a fluoroquinolone compared with nonfluoroquinolones: clinical implications and a review of kinetics of kill studies. Advances in therapy 24:1098-1111; Granet D B, Dorfman M, Stroman D, Cockrum P. 2008. A multicenter comparison of polymyxin B sulfate/trimethoprim ophthalmic solution and moxifloxacin in the speed of clinical efficacy for the treatment of bacterial conjunctivitis. Journal of pediatric ophthalmology and strabismus 45:340-349; and Price F W, Jr., Dobbins K, Zeh W. 2002. Penetration of topically administered ofloxacin and trimethoprim into aqueous humor. Journal of ocular pharmacology and therapeutics: the official journal of the Association for Ocular Pharmacology and Therapeutics 18:445-453.

SUMMARY OF THE INVENTION

The present invention provides an anti-bacterial composition comprising as active agents 1) a composition A comprising polymyxin B and trimethoprim; and 2) one antibiotic agent that is a) rifamycin, or a rifamycin derivative selected from the group consisting of rifampicin (or rifampin), rifabutin, rifapentine, rifalazil and rifaximin or b) one selected from the group consisting of pefloxacin mesy late, sparfloxacin, sarafloxacin HCl, tobramycin, lomefloxacin, besifloxacin, danofloxacin mesylate, enrofloxacin, nadifloxacin and clinafloxacin and one or more pharmaceutically acceptable carriers or excipients. In one embodiment, the weight ratio between the composition A and the antibiotic agent is from about 1:1000 to about 1000:1. In one embodiment, the weight ratio between the composition A and the antibiotic agent is from about 1:500 to about 500:1. In one embodiment, the weight ratio between the composition A and the antibiotic agent is from about 1:100 to about 100:1.

In one embodiment of the present invention, the composition A of the antibacterial composition described herein comprises Polytrim. In one embodiment of the present invention, the composition A of the antibacterial composition described herein consists of polymyxin B and trimethoprim.

Also in one embodiment of the present invention, the antibiotic agent of the antibacterial composition described herein is rifampicin.

In another embodiment of the present invention, the composition A consists of polymyxin B and trimethoprim and the antibiotic agent is rifampicin. Also in another embodiment of the present invention, the antibacterial composition consists of polymyxin B, trimethoprim and rifampicin.

Yet in another embodiment of the present invention, the antibacterial composition comprises Polytrim and rifampicin.

Yet in another embodiment of the present invention, Polytrim and rifampicin are the only active agents.

Also described in this application is that the total concentration of the composition A and the antibiotic agent in the antibacterial composition of the present invention as described herein is from about 1 wt. % to about 50 wt. % per unit of the antibacterial composition. Preferably, the total concentration is about 50 weight percentage (wt. %), about 40 wt. %, about 30 wt. %, about 25 wt. %, about 20 wt. %, about 15 wt. %, about 10 wt. %, about 5 wt. %, about 3 wt. %, about 2 wt. %, about 1 wt. % per unit of the antibacterial composition.

The antibacterial composition of the present invention described herein can be used for administration to treat bacterial infection in ocular tissue, otic tissue, nasal tissue, skin, or wound in a subject.

In another embodiment, the antibacterial composition of the present invention as described herein above is formulated into a topical pharmaceutical composition. The topical pharmaceutical composition comprises the antibacterial composition in various embodiments as defined herein above and one or more pharmaceutically acceptable carriers or excipients.

In another aspect, the present invention provides a topical pharmaceutical composition comprising as active agents 1) a composition A comprising polymyxin B and trimethoprim; and 2) one antibiotic agent that is a) rifamycin, or a rifamycin derivative selected from the group consisting of rifampicin (or rifampin), rifabutin, rifapentine, rifalazil and rifaximin or b) one selected from the group consisting of pefloxacin mesylate, sparfloxacin, sarafloxacin HCl, tobramycin, lomefloxacin, besifloxacin, danofloxacin mesylate, enrofloxacin, nadifloxacin and clinafloxacin and one or more pharmaceutically acceptable carriers or excipients, wherein the concentration of the composition A is from about 0.001 wt. % to about 8 wt. % per unit of the topical pharmaceutical composition and the concentration of the antibiotic agent is from about 0.001 wt. % to about 10 wt. % per unit of the topical pharmaceutical composition. In one embodiment, the concentration of the composition A is from about 0.015 wt. % to about 1 wt. % per unit of the topical pharmaceutical composition and the concentration of the antibiotic agent is from about 0.015 wt. % to about 2 wt. % per unit of the topical pharmaceutical composition. In one further embodiment, the weight ratio between the composition A and the antibiotic agent is from about 1:1000 to about 1000:1. In one embodiment, the weight ratio between the composition A and the antibiotic agent is from about 1:500 to about 500:1. In one embodiment, the weight ratio between the composition A and the antibiotic agent is from about 1:100 to about 100:1.

In one embodiment, the composition A of the topical pharmaceutical composition comprises Polytrim. In one embodiment, the antibiotic agent of the topical pharmaceutical composition is rifampicin. In one embodiment, the composition A consists of as active agents polymyxin B and trimethoprim and the antibiotic agent is rifampicin. In one embodiment, the composition A comprises Polytrim and the antibiotic agent is rifampicin. In one embodiment of the present invention, Polytrim and rifampicin are the only active agents.

In one embodiment, the antibacterial composition or the topical pharmaceutical composition as described herein is for treating ocular, otic, nasal, skin or wound infection in a subject. In one embodiment, the infection is bacterial infection. In one embodiment, the bacterial ocular infection is bacterial keratitis, bacterial conjunctivitis, or bacterial endothalmitis. In further embodiment, the antibacterial composition or the topical pharmaceutical composition is for treating surface ocular bacterial infections, including acute bacterial conjunctivitis, and blepharoconjunctivitis, caused by susceptible strains of the following microorganisms: *Staphylococcus aureus, Staphylococcus epidermidis, Streptococcus pneumonia, Streptococcus viridans, Haemophilus influenza, Acinetobacter* sp., *Morexcella* sp., and *Pseudomonas aeruginosa*, etc.

In one embodiment, the antibacterial composition or the topical pharmaceutical composition of the present invention may take the form of a cream, a lotion, an ointment, a hydrogel, a colloid, a gel, a foam, an oil, a milk, a suspension, a wipe, a sponge, a solution, an emulsion, a paste, a patch, a pladget, a swab, a dressing, a spray or a pad.

In one embodiment, the topical pharmaceutical composition of the present invention is a topical ophthalmic pharmaceutical composition preferably in the form of a solution or suspension, an emulsion, an ointment, a cream, a gel, or a sustained release vehicle, such as an ocular insert.

In another aspect, the present invention provides a method of treating a bacterial infection in a subject comprising administering to the subject separately, simultaneously or sequentially a therapeutically effective amount of the antibacterial composition described herein throughout the specification. In one embodiment, the antibacterial composition is formulated into a topical pharmaceutical composition. In one embodiment, the topical pharmaceutical composition is a formulation for treating ocular, otic, nasal, skin or wound infection. In one embodiment, the bacterial infection is from Gram-positive or Gram-negative bacteria or the combination of both.

In one embodiment, the topical pharmaceutical composition is an ophthalmic formulation for treating bacterial ocular infection. Non-limiting examples of the bacterial ocular infection are bacterial keratitis, bacterial conjunctivitis, or bacterial endothalmitis. In one example, the ophthalmic formulation is for treating surface ocular bacterial infections, including acute bacterial conjunctivitis, and blepharoconjunctivitis, caused by susceptible strains of the following microorganisms: *Staphylococcus aureus, Staphylococcus epidermidis, Streptococcus pneumonia, Streptococcus viridans, Haemophilus influenza* and *Pseudomonas aeruginosa*, etc.

In one embodiment, the present invention provides a method of decolonizing a bacterial organism comprising contacting the bacterial organism separately, simultaneously or sequentially with the antibacterial composition described herein throughout the specification.

In one embodiment, the present invention provides a method of decolonizing a bacterial organism comprising contacting the bacterial organism separately, simultaneously or sequentially with the topical pharmaceutical composition described herein throughout the specification.

In one embodiment, the present invention provides a method of destroying or disrupting or inhibiting or reducing biofilm formation a bacterial organism comprising contacting the bacterial organism separately, simultaneously or sequentially with the antibacterial composition described herein throughout the specification.

In one embodiment, the present invention provides a method of destroying or disrupting or inhibiting or reducing biofilm formation a bacterial organism comprising contacting the bacterial organism separately, simultaneously or sequentially with the topical pharmaceutical composition described herein throughout the specification.

BRIEF DESCRIPTION OF THE DRAWINGS

FIG. 1, comprising

FIG. 2, comprising

FIG. 3, comprising

FIG. 4, comprising

DETAILED DESCRIPTION

Figure 1A:
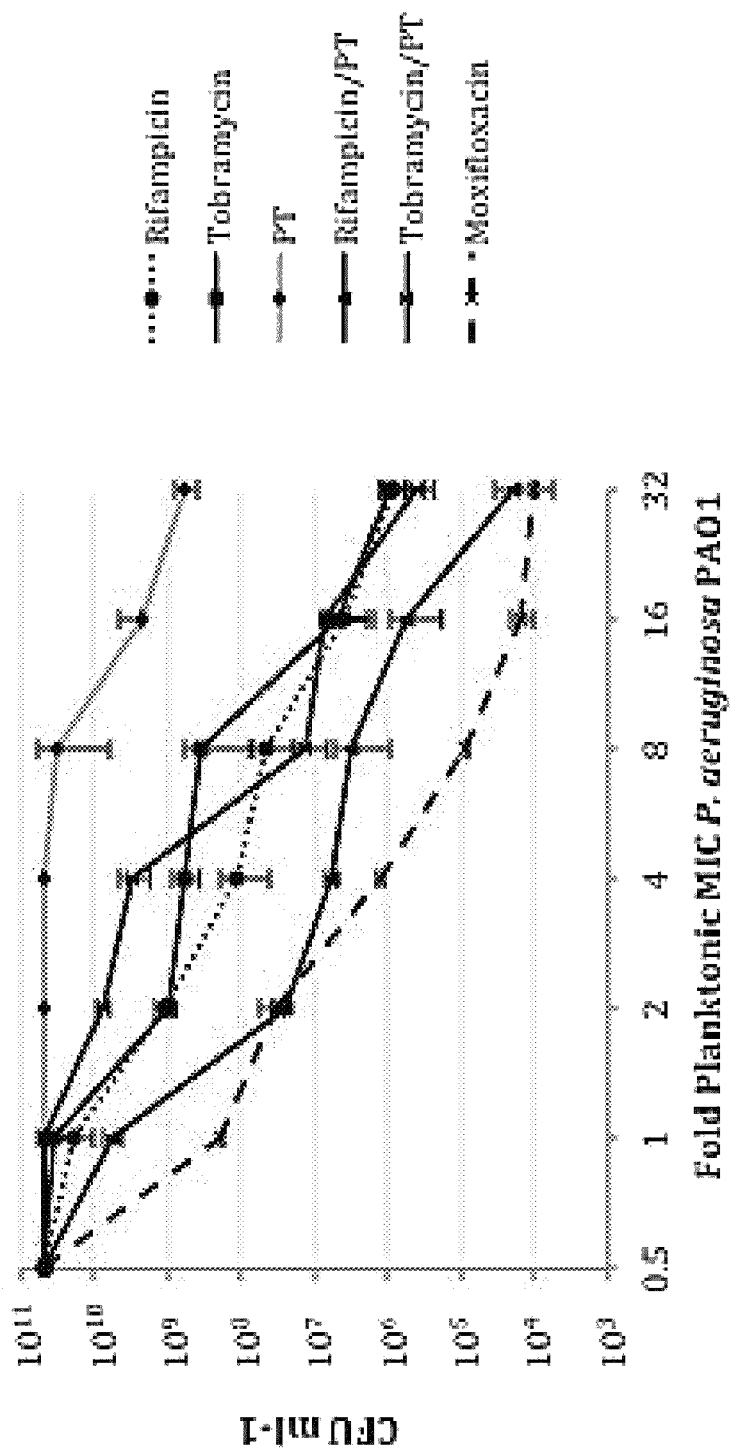
FIG. 1A and FIG. 1B, shows antibiofilm activity of moxifloxacin, tobramycin, polymyxin B/trimethoprim, rifampicin, polymyxin B/trimethoprim+rifampicin, and polymyxin B/trimethoprim+tobramycin against *P. aeruginosa* PA01 (FIG. 1A) and *S. aureus* UAMS-1 (FIG. 1B).
Figure 1B:
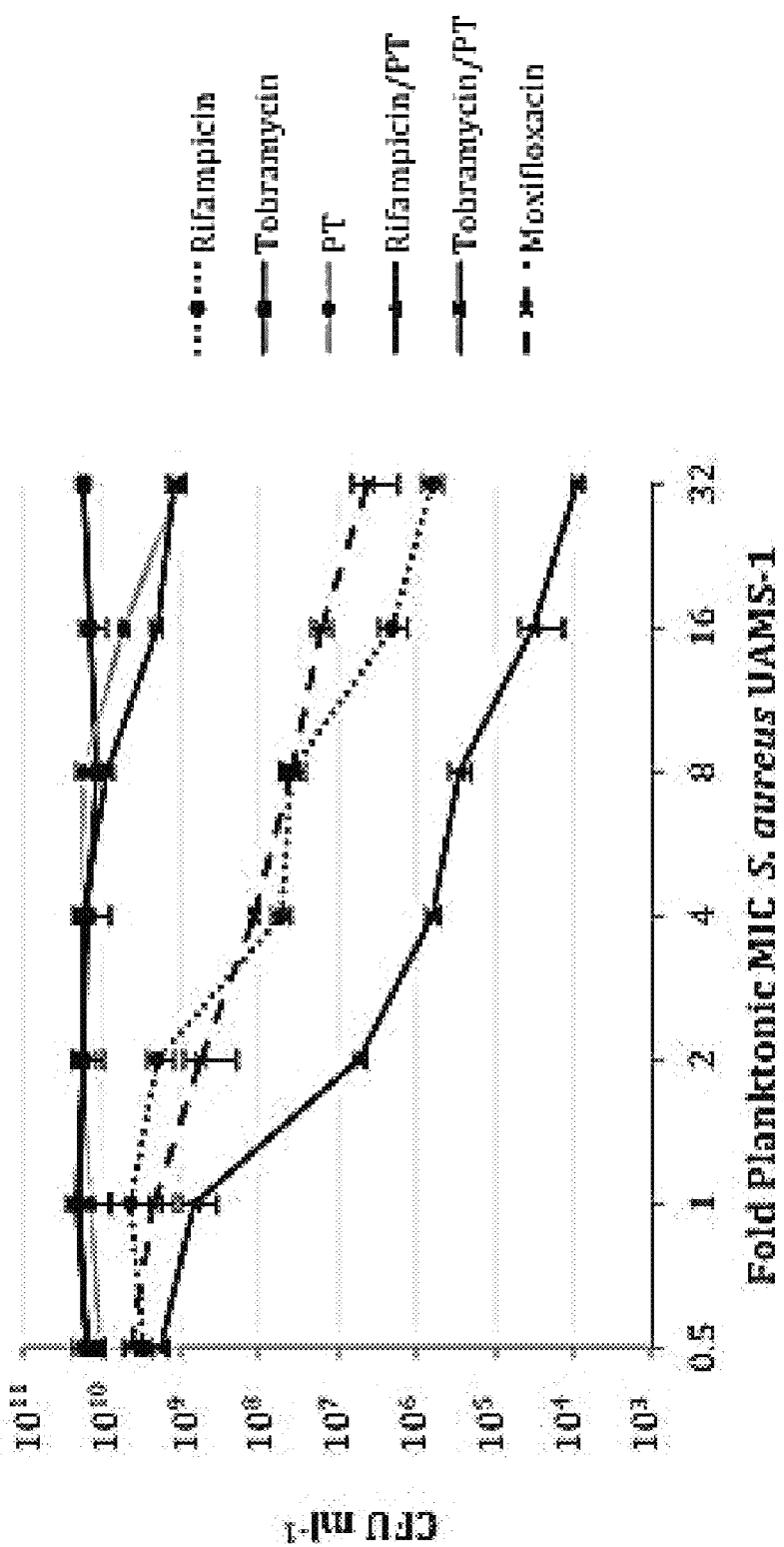

For purposes of interpreting this specification, the following definitions will apply and whenever appropriate, terms used in the singular will also include the plural and vice versa.

As used herein, the term "microbial organism" or "microbe," or "microbial," or "microorganism" refers to a domain (Bacteria) of prokaryotic round, spiral, or rod-shaped single-celled, multi-celled, or acelled microorganisms that may lack cell walls or are Gram-positive or Gram-negative or alteration thereof (i.e. *Mycobacterium*) if they have cell walls, that are often aggregated into colonies or motile by means of flagella, that typically live in soil, water, organic matter, or the bodies of plants and animals, that are usually autotrophic, saprophytic, or parasitic in nutrition, and that are noted for their biochemical effects and pathogenicity. The term is intended to encompass prokaryotic or eukaryotic cells or organisms having a microscopic size and includes bacteria, viruses, archaea and eubacteria of all species as well as eukaryotic microorganisms such as yeast and fungi. The term also includes cell cultures of any species that can be cultured for the production of a biochemical. In one non-limiting example, the activity of a microbial organism can be measured by calculating the log reduction in number of the microorganism.

As used herein, the term "bacteria" includes, but is not limited to, references to organisms of the following classes and specific types:

1) Gram-positive cocci, such as Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*);

2) Streptococci (e.g. beta-haemolytic, pyogenic streptococci (such as *Strept. agalactiae, Strept. canis, Strept. dysgalactiae dysgalactiae, Strept. dysgalactiae equisimilis, Strept. equi equi, Strept. equi zooepidemicus, Strept. iniae, Strept porcinus* and *Strept. pyogenes*), microaerophilic, pyogenic streptococci (*Streptococcus "milleri"*, such as *Strept. anginosus, Strept constellatus constellatus, Strept. constellatus pharyngidis* and *Strept. intermedius*), oral streptococci of the *"mitis"* (alpha-haemolytic—*Streptococcus "viridans"*, such as *Strept. mitis, Strept. oralis,* Strept. *sanguinis, Strept. cristatus, Strept. gordonii* and *Strept. parasanguinis*), *"salivarius"* (non-haemolytic, such as *Strept. salivarius* and *Strept. vestibularis*) and "mutans" (tooth-surface streptococci, such as *Strept. criceti, Strept. mutans, Strept. ratti* and *Strept sobrinus*) groups, *Strept. acidominimus, Strept. bovis, Strept. faecalis, Strept. equinus, Strept. pneumoniae* and *Strept. suis*, or Streptococci alternatively classified as Group A, B, C, D, E, G, L, P, U or V *Streptococcus*);

3) Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri;*

4) Bacillaceae, such as *Bacillus anthracis, Bacillus subtilis, Bacillus thuringiensis, Bacillus stearothermophilus* and *Bacillus cereus;*

5) Enterobacteriaceae, such as *Escherichia coli, Enterobacter* (e.g. *Enterobacter aerogenes, Enterobacter agglomerans* and *Enterobacter cloacae*), *Citrobacter* (such as *Citrob. freundii* and *Citrob. divernis*), *Hafnia* (e.g. *Hafnia alvei*), *Erwinia* (e.g. *Erwinia persicinus*), *Morganella morganii, Salmonella* (*Salmonella enterica* and *Salmonella typhi*), *Shigella* (e.g. *Shigella dysenteriae, Shigella flexneri, Shigella boydii* and *Shigella sonnei*), *Klebsiella* (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*), *Proteus* (e.g. *Pr. mirabilis, Pr. rettgeri* and *Pr. vulgaris*), *Providencia* (e.g. *Providencia alcalifaciens, Providencia rettgeri* and *Providencia stuartii*), *Serratia* (e.g. *Serratia marcescens* and *Serratia liquifaciens*), and *Yersinia* (e.g. *Yersinia enterocolitica, Yersinia pestis* and *Yersinia pseudotuberculosis*);

6) Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae,* Entero-

*coccus malodoratus, Enterococcus mundtii, Enterococcus pseudoavium, Enterococcus raffinosus* and *Enterococcus solitarius*);

7) *Helicobacter* (e.g. *Helicobacter pylori, Helicobacter cinaedi* and *Helicobacter fennelliae*);
8) *Acinetobacter* (e.g. *A. baumannii, A. calcoaceticus, A. haemolyticus, A. johnsonii, A. junii, A. Iwoffi* and *A. radioresistens*);
9) *Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzeri*);
10) *Bacteroides fragilis*;
11) *Peptococcus* (e.g. *Peptococcus niger*);
12) *Peptostreptococcus*;
13) *Clostridium* (e.g. *C. perfringens, C. difficile, C. botulinum, C. tetani, C. absonum, C. argentinense, C. baratii, C. bifermentans, C. beijerinckii, C. butyricum, C. cadaveris, C. camis, C. celatum, C. clostridioforme, C. cochlearium, C. cocleatum, C. fallax, C. ghonii, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tertium*);
14) *Mycoplasma* (e.g. *M. pneumoniae, M. hominis, M. genitalium* and *M. urealyticum*);
15) Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*); *Haemophilus* (e.g. *Haemophilus influenzae, Haemophilus ducreyi, Haemophilus aegyptius, Haemophilus parainfluenzae, Haemophilus haemolyticus* and *Haemophilus parahaemolyticus*);
16) *Actinobacillus* (e.g. *Actinobacillus actinomycetemcomitans, Actinobacillus equuli*;
17) *Actinobacillus hominis, Actinobacillus lignieresii, Actinobacillus suis* and *Actinobacillus ureae*;
18) *Actinomyces* (e.g. *Actinomyces israelii*);
19) *Brucella* (e.g. *Brucella abortus, Brucella canis, Brucella melintensis* and *Brucella suis*);
20) *Campylobacter* (e.g. *Campylobacter jejuni, Campylobacter coli, Campylobacter lari* and *Campylobacter fetus*);
21) *Listeria monocytogenes*;
22) *Vibrio* (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*);
23) *Erysipelothrix rhusopathiae*;
24) Corynebacteriaceae (e.g. *Corynebacterium diphtheriae, Corynebacterium jeikeum* and *Corynebacterium urealyticum*);
25) Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*); *Pasteurella* (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida* septica, *Pasteurella pneumotropica* and *Pasteurella stomatis*);
26) *Bordetella* (e.g. *Bordetella bronchiseptica, Bordetella hinzii, Bordetella holmseii, Bordetella parapertussis, Bordetella pertussis* and *Bordetella trematum*);
27) Nocardiaceae, such as *Nocardia* (e.g. *Nocardia asteroides* and *Nocardia brasiliensis*);
28) *Rickettsia* (e.g. *Ricksettsii* or *Coxiella burnetii*);
29)
30) *Legionella* (e.g. *Legionalla anisa, Legionalla birminghamensis, Legionalla bozemanii, Legionalla cincinnatiensis, Legionalla dumoffii, Legionalla feeleii, Legionalla gormanii, Legionalla hackeliae, Legionalla israelensis, Legionalla jordanis, Legionalla lansingensis, Legionalla longbeachae, Legionalla maceachemii, Legionalla micdadei, Legionalla oakridgensis, Legionalla pneumophila, Legionalla sainthelensi, Legionalla tucsonensis*;
31) *Legionalla wadsworthii*;
32) *Moraxella catarrhalis*;
33) *Cyclospora cayetanensis*;
34) *Entamoeba histolytica*;
35) *Giardia lamblia*;
36) *Trichomonas vaginalis*;
37) *Toxoplasma gondii*;
38) *Stenotrophomonas maltophilia*;
39) *Burkholderia cepacia; Burkholderia mallei* and *Burkholderia pseudomallei*;
40) *Francisella tularensis*;
41) *Gardnerella* (e.g. *Gardneralla vaginalis* and *Gardneralla mobiluncus*); *Streptobacillus moniliformis*;
42) Flavobacteriaceae, such as *Capnocytophaga* (e.g. *Capnocytophaga canimorsus, Capnocytophaga cynodegmi, Capnocytophaga gingivalis, Capnocytophaga* granulosa, *Capnocytophaga haemolytica, Capnocytophaga ochracea* and *Capnocytophaga sputigena*);
43) *Bartonella* (*Bartonella bacilliformis, Bartonella clarridgeiae, Bartonella elizabethae, Bartonella henselae, Bartonella quintana* and *Bartonella vinsonii arupensis*);
44) *Leptospira* (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*);
45) *Spirillium* (e.g. *Spirillum minus*);
46) *Baceteroides* (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*);
47) *Prevotella* (e.g. *Prevotella bivia, Prevotella buccae, Prevotella corporis, Prevotella dentalis* (*Mitsuokella dentalis*), *Prevotella denticola, Prevotella disiens, Prevotella enoeca, Prevotella heparinolytica, Prevotella intermedia, Prevotella loeschii, Prevotella melaninogenica, Prevotella nigrescens, Prevotella oralis, Prevotella oris, Prevotella oulora, Prevotella tannerae, Prevotella venoralis* and *Prevotella zoogleoformans*); *Porphyromonas* (e.g. *Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*);
48) *Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*);
49) *Chlamydia* (e.g. *Chlamydia trachomatis*);
50) *Cryptosporidium* (e.g. *C. parvum, C. hominis, C. canis, C. felis, C. meleagridis* and *C. muris*);
51) *Chlamydophila* (e.g. *Chlamydophila abortus* (*Chlamydia psittaci*), *Chlamydophila pneumoniae* (*Chlamydia pneumoniae*) and *Chlamydophila psittaci* (*Chlamydia psittaci*));
52) *Leuconostoc* (e.g. *Leuconostoc citreum, Leuconostoc cremoris, Leuconostoc dextranicum, Leuconostoc lactis, Leuconostoc mesenteroides* and *Leuconostoc pseudomesenteroides*);
53) *Gemella* (e.g. *Gemella bergeri, Gemella haemolysans, Gemella morbillorum* and *Gemella sanguinis*); and
54) *Ureaplasma* (e.g. *Ureaplasma parvum* and *Ureaplasma urealyticum*).

As used herein, the term "microbial colonization" refers to the formation of compact population groups of the same type of microorganism (such as bacteria), such as the colonies that develop when a microbial (such as bacterial) cell begins reproducing. The microbial colonization (such as bacterial colonization) may or may not cause disease symptoms. Decolonization refers to a reduction in the number of microbial (such as bacterial) organisms present. When the microbial organisms are completely decolonized, the microbial organisms have been eradicated and are non-detectable.

As used herein, the term "biofilm" refers to matrix-enclosed microbial (such as bacteria) accretions to biological or non-biological surfaces in which microorganisms are dispersed and/or form colonies. The biofilm typically is made of polysaccharides and other macromolecules. Biofilm formation represents a protected mode of growth that allows cells to survive in hostile environments.

As used herein, the term "biofilm formation" is intended to include the formation, growth, and modification of microbes contained with biofilm structures, as well as the synthesis and maintenance of a polysaccharide matrix of the biofilm structures. Also within the scope of this term is formation of protein-based biofilms that do not secrete polysaccharide in the matrix but which comprise proteins that permit bacteria to form biofilm architecture.

As used herein, the term "rifamycin" refers to a group of antibiotics that are synthesized either naturally by the bacterium *Amycolatopsis rifamycinica* or artificially. The rifamycin group includes the "classic" rifamycin drugs as well as the rifamycin derivatives rifampicin (or rifampin), rifabutin, rifapentine, rifalazil and rifaximin.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "therapeutically effective amount" of compounds of the present invention refers to an amount of the compounds of the present invention that will elicit the biological or medical response of a subject, or ameliorate symptoms, slow or delay disease progression, or prevent a disease, etc. In one embodiment, the term refers to the amount that inhibits or reduces microbial colonization or infection. In one embodiment, the term refers to the amount that inhibits or reduces bacterial infection, or prevent or destroying the formation of bacterial biofilms. When applied to an individual active ingredient, administered alone, the term refers to that ingredient alone. When applied to a combination, the term refers to combined amounts of the active ingredients that result in the therapeutic effect, whether administered in combination, serially or simultaneously.

As used herein, the term "pharmaceutically acceptable carrier or excipient" refers to a carrier medium or an excipient which does not interfere with the effectiveness of the biological activity of the active ingredient(s) of the composition and which is not excessively toxic to the host at the concentrations at which it is administered. In the context of the present invention, a pharmaceutically acceptable carrier or excipient is preferably suitable for topical formulation. The term includes, but is not limited to, a solvent, a stabilizer, a solubilizer, a tonicity enhancing agent, a structure-forming agent, a suspending agent, a dispersing agent, a chelating agent, an emulsifying agent, an anti-foaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof. The use of such agents for the formulation of pharmaceutically active substances is well known in the art (see, for example, "Remington's Pharmaceutical Sciences", E. W. Martin, 18$^{th}$ Ed., 1990, Mack Publishing Co.: Easton, Pa., which is incorporated herein by reference in its entirety).

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder. The term "treating" or "treatment" also refers to a reduction in the severity of one or more symptoms by about 10%, about 20%, about 30%, about 40%, about 50%, about 60%, about 70%, about 80%, about 90% or about 100%.

As used herein, the term "topical administration" refers to the delivery to a subject by contacting the formulation directly to a surface or localized region of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition.

As used herein, the term "topical composition" (synonymously, "topical formulation") is used herein to refer to a pharmaceutical preparation intended for topical or local application to an afflicted region of a subject in need thereof, and includes such dosage forms as gel, cream, ointment, emulsion, suspension, solution, drops, lotion, paint, pessary, douche, suppository, troche, spray, sponge, film, or foam. Preferably, the topical formulation is in the form of a cream, a gel, or an ointment.

As used herein, the term "comprising" means "including," "containing," "comprehending," "consisting essentially of," or "consisting of." It is used herein to encompass all the specifically mentioned features as well as optional, additional, unspecified ones, whereas the term "consisting of" only includes those features as specified in the claim. Therefore, "comprising" includes as a limiting case the composition specified by "consisting of" or "consisting essentially of". In one example, the term "comprising" only includes those features specified in the claim.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

As used herein, the term "about" refers to within 10%, preferably within 5%, and more preferably within 1% of a given value or range. Alternatively, the term "about" refers to within an acceptable standard error of the mean, when considered by one of ordinary skill in the art.

The present invention provides a composition having enhanced antimicrobial efficacy and effective for inhibiting, reducing or treating microbial infections such as bacterial infections, and/or for decolonizing a microbial organism and/or for destroying, disrupting, inhibiting or reducing bacterial biofilm formation. It is our surprising and unexpected discovery that a composition comprising a combination of 1) a composition A comprising polymyxin B and trimethoprim; and 2) one antibiotic agent that is a) rifamycin, or a rifamycin derivative selected from the group consisting of rifampicin (or rifampin), rifabutin, rifapentine, rifalazil and rifaximin or b) one selected from the group consisting of pefloxacin mesylate, sparfloxacin, sarafloxacin HCl, tobramycin, lomefloxacin, besifloxacin, danofloxacin mesylate, enrofloxacin, nadifloxacin and clinafloxacin, when used to treat a microbial (such as bacterial) organism, demonstrates synergistic effect against a microbial (such as bacterial), colonization or infection or biofilm formation. As used herein, the term "synergistic" refers to the effect obtained by combining compounds and/or agents that is greater than the effect obtained by the separate addition of each compound. The combination treatment of the present invention has shown a synergistic effect as measured by, for example, the extent of the response, the duration of response, the response rate, the stabilization rate, the duration of stabilization, the time to reduce or clear the infections, the time to eradicate the microorganisms, to that achievable on dosing one or other of the components of the combination treatment at its conventional dose. For example, the effect of the combination treatment of the present invention is synergistic because the combination treatment is therapeutically superior to the effect achievable with one component alone. The superior effect can be improved reduction in drug resistance from the microbial organisms, the extent to which the microbial organisms are reduced or eradicated and become non-detectable by the combination treatment. Also for example, the effect of the combination treatment of the present invention is synergistic because it takes shorter time to kill the microorganisms. Also for example, the effect of the combination treatment of the present invention is synergistic because the combination treatment offers broader spectrum of antimicrobial activities than those with one component alone. Also for example, the effect of the combination treatment of the present invention is synergistic because one of the components in the composition described in this invention is dosed at its conventional dose and the other component(s) is/are dosed at a reduced dose and the therapeutic effect, as measured by, for example, the extent of the killing and/or inhibiting growth of the microorganisms such as bacteria, the time to kill and/or inhibit growth of the microorganisms such as bacteria, or the time to destroy or inhibit microbial colonies, or the time to disrupt or inhibit or reduce biofilm formation or growth, is equivalent to that achievable on dosing conventional amounts of the components of the combination treatment.

In one aspect, the present invention provides an antibacterial composition comprising as active agents 1) a composition A comprising polymyxin B and trimethoprim; and 2) one antibiotic agent that is a) rifamycin, or a rifamycin derivative selected from the group consisting of rifampicin (or rifampin), rifabutin, rifapentine, rifalazil and rifaximin or b) one selected from the group consisting of pefloxacin mesylate, sparfloxacin, sarafloxacin HCl, tobramycin, lomefloxacin, besifloxacin, danofloxacin mesylate, enrofloxacin, nadifloxacin and clinafloxacin and one or more pharmaceutically acceptable carriers or excipients. In one embodiment, the weight ratio between the composition A and the antibiotic agent is from about 1:1000 to about 1000:1. In one embodiment, the weight ratio between the composition A and the antibiotic agent is from about 1:500 to about 500:1. In one embodiment, the weight ratio between the composition A and the antibiotic agent is from about 1:100 to about 100:1. In one embodiment, the weight ratio between the composition A and the antibiotic agent is from about 1:1 to about 50:1. In one embodiment, the weight ratio between the composition A and the antibiotic agent is from about 5:1 to about 25:1. In one embodiment, the weight ratio between the composition A and the antibiotic agent is about 1:1, about 1:10, about 1:15, about 1:20, about 1:30, about 1:40, about 1:50, about 1:60, about 1:70, about 1:80, about 1:90, about 1:100, about 1:125, about 1:150, about 1:175, about 1:200, about 1:250, about 1:300, about 1:350, about 1:400, about 1:450, about 1:500, about 1:550, about 1:600, about 1:650, about 1:700, about 1:750, about 190:1, about 1:800, about 1:850, about 1:900, about 1:950, or about 1:1000. In one embodiment, the weight ratio between the composition A and the antibiotic agent is about 2:1, about 3:1, about 4:1, about 5:1, about 8:1, about 10:1, about 15:1, about 20:1, about 25:1, about 30:1, about 40:1, about 50:1, about 60:1, about 70:1, about 80:1, about 90:1, about 100:1, about 125:1, about 150:1, about 175:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, or about 1000:1.

Polymyxin B and trimethoprim of the composition A are antibacterial agents. Polymyxin B, a cyclic lipopeptide antibiotic, is bactericidal for a variety of gram-negative organisms, especially *Pseudomonas aeruginosa*. It increases the permeability of the bacterial cell membrane by interacting with the phospholipid components of the membrane. Trimethoprim is a synthetic antibacterial drug active against a wide variety of aerobic gram-positive and gram-negative ophthalmic pathogens. Trimethoprim blocks the production of tetrahydrofolic acid from dihydrofolic acid by binding to and reversibly inhibiting the enzyme dihydrofolate reductase. This binding is stronger for the bacterial enzyme than for the corresponding mammalian enzyme and therefore selectively interferes with bacterial biosynthesis of nucleic acids and proteins. Researchers have shown that Polymyxin B is active against the following non-limiting bacterial pathogens: *Pseudomonas aeruginosa, Escherichia coli, Klebsiella pneumoniae, Enterobacter aerogenes* and *Haemophilus influenza*, etc. Trimethoprim is known to be active against the following non-limiting bacterial pathogens: *Staphylococcus aureus* and *Staphylococcus epidermidis, Streptococcus pyogenes, Streptococcus faecalis, Streptococcus pneumoniae, Haemophilus influenzae, Haemophilus aegyptius, Escherichia coli, Klebsiella pneumoniae, Proteus mirabilis* (indole-negative), *Proteus vulgaris* (indole-positive), *Enterobacter aerogenes* and *Serratia marcescens*, etc.

Accordingly, in one embodiment of the present invention, the composition A consists of polymyxin B and trimethoprim. Also in another embodiment of the present invention, the antibacterial composition consists of as active agents polymyxin B, trimethoprim and rifampicin.

Polymyxin B and trimethoprim of the composition A are also two active components of the drug named Polytrim. Polytrim is an ophthalmic solution containing 10,000 units/mL of polymyxin B sulfate, 1 mg/mL of trimethoprim sulfate and pharmaceutically acceptable excipients or carriers. See also FDA NDA application number N050567. Polytrim ophthalmic solution is indicated in the treatment of surface ocular bacterial infections. Non-limiting examples of such infections include acute bacterial conjunctivitis, and blepharoconjunctivitis, caused by susceptible strains of the following microorganisms: *Staphylococcus aureus, Staphylococcus epidermidis, Streptococcus pneumoniae, Streptococcus viridans, Haemophilus influenzae* and *Pseudomonas aeruginosa*, etc.

Therefore in one embodiment of the present invention, the composition A of the antibacterial composition described herein comprises Polytrim. In one embodiment, the weight ratio between Polytrim and the antibiotic agent is from about 1:1000 to about 1000:1. In one embodiment, the weight ratio between Polytrim and the antibiotic agent is from about 1:500 to about 500:1. In one embodiment, the weight ratio between Polytrim and the antibiotic agent is from about 1:100 to about 100:1. In one embodiment, the weight ratio between Polytrim and the antibiotic agent is from about 1:1 to about 50:1. In one embodiment, the weight ratio between Polytrim and the antibiotic agent is from about 5:1 to about 25:1. In one embodiment, the weight ratio between Polytrim and the antibiotic agent is about 1:1, about 1:10, about 1:15, about 1:20, about 1:30, about 1:40, about 1:50, about 1:60, about 1:70, about 1:80, about 1:90, about 1:100, about 1:125, about 1:150, about 1:175, about 1:200, about 1:250, about 1:300, about 1:350, about 1:400, about 1:450, about 1:500, about 1:550, about 1:600, about 1:650, about 1:700, about 1:750, about 1:800, about 1:850, about 1:900, about 1:950, or about 1:1000. In one embodiment, the weight ratio between Polytrim and the antibiotic agent is about 2:1, about 3:1, about 4:1, about 5:1, about 8:1, about 10:1, about 15:1, about 20:1, about 25:1, about 30:1, about 40:1, about 50:1, about 60:1, about 70:1, about 80:1, about 90:1, about 100:1, about 125:1, about 150:1, about 175:1, about 190:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, or about 1000:1.

Also in one embodiment of the present invention, the antibiotic agent of the antibacterial composition described herein is rifampicin. In one embodiment, the weight ratio between the composition A and rifampicin is from about 1:1000 to about 1000:1. In one embodiment, the weight ratio between the composition A and rifampicin is from about 1:500 to about 500:1. In one embodiment, the weight ratio between the composition A and rifampicin is from about 1:100 to about 100:1. In one embodiment, the weight ratio between the composition A and rifampicin is from about 1:1 to about 50:1. In one embodiment, the weight ratio between the composition A and rifampicin is from about 5:1 to about 25:1. In one embodiment, the weight ratio between the composition A and rifampicin is about 1:1, about 1:10, about 1:15, about 1:20, about 1:30, about 1:40, about 1:50, about 1:60, about 1:70, about 1:80, about 1:90, about 1:100, about 1:125, about 1:150, about 1:175, about 190:1, about 1:200, about 1:250, about 1:300, about 1:350, about 1:400, about 1:450, about 1:500, about 1:550, about 1:600, about 1:650, about 1:700, about 1:750, about 1:800, about 1:850, about 1:900, about 1:950, or about 1:1000. In one embodiment, the weight ratio between the composition A and rifampicin is about 2:1, about 3:1, about 4:1, about 5:1, about 8:1, about 10:1, about 15:1, about 20:1, about 25:1, about 30:1, about 40:1, about 50:1, about 60:1, about 70:1, about 80:1, about 90:1, about 100:1, about 125:1, about 150:1, about 175:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, or about 1000:1.

Yet in another embodiment of the present invention, the antibacterial composition comprises Polytrim and rifampicin. In another embodiment of the present invention, Polytrim and rifampicin are the only active agents. In one embodiment, the weight ratio between Polytrim and rifampicin is from about 1:1000 to about 1000:1. In one embodiment, the weight ratio between Polytrim and rifampicin is from about 1:500 to about 500:1. In one embodiment, the weight ratio between Polytrim and rifampicin is from about 1:100 to about 100:1. In one embodiment, the weight ratio between Polytrim and rifampicin is from about 1:1 to about 50:1. In one embodiment, the weight ratio between Polytrim and rifampicin is from about 5:1 to about 25:1. In one embodiment, the weight ratio between Polytrim and rifampicin is about 1:1, about 1:10, about 1:15, about 1:20, about 1:30, about 1:40, about 1:50, about 1:60, about 1:70, about 1:80, about 1:90, about 1:100, about 1:125, about 1:150, about 1:175, about 1:200, about 1:250, about 1:300, about 1:350, about 1:400, about 1:450, about 1:500, about 1:550, about 1:600, about 1:650, about 1:700, about 1:750, about 1:800, about 1:850, about 1:900, about 1:950, or about 1:1000. In one embodiment, the weight ratio between Polytrim and rifampicin is about 2:1, about 3:1, about 4:1, about 5:1, about 8:1, about 10:1, about 15:1, about 20:1, about 25:1, about 30:1, about 40:1, about 50:1, about 60:1, about 70:1, about 80:1, about 90:1, about 100:1, about 125:1, about 150:1, about 175:1, about 190:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, or about 1000:1.

Also described in this application is that the total concentration of the composition A and the antibiotic agent in the antibacterial composition of the present invention as described herein is from about 1 wt. % to about 50 wt. % per unit of the antibacterial composition. Preferably, the total concentration is about 50 weight percentage (wt. %), about 40 wt. %, about 30 wt. %, about 25 wt. %, about 20 wt. %, about 15 wt. %, about 10 wt. %, about 5 wt. %, about 3 wt. %, about 2 wt. %, about 1 wt. % per unit of the antibacterial composition.

The antibacterial composition of the present invention described herein can be used for administration to treat bacterial infection in ocular tissue, otic tissue, nasal tissue, skin or wound in a subject. In one embodiment, the bacterial infection is from Gram-positive or Gram-negative bacteria or a combination of both. In one embodiment the bacterial infection is from one selected from *Staphylococcus* spp., e.g. *Staphylococcus aureus, Staphylococcus epidermidis; Enterococcus* spp., e.g. *Enterococcus faecalis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp.; *Streptococcus pyogenes; Listeria* spp.; *Pseudomonas* spp.; *Mycobacterium* spp., e.g. *Mycobacterium tuberculosis; Enterobacter* spp.; *Campylobacter* spp.; *Salmonella* spp.; *Streptococcus* spp., e.g. *Streptoccus* Group A or B, *Streptoccocus pneumoniae; Helicobacter* spp., e.g. *Helicobacter pylori; Neisseria* spp., e.g. *Neisseria* gonorrhea, *Neisseria meningitidis; Borrelia burgdorferi; Shigella* spp., e.g. *Shigella flexneri; Escherichia coli; Haemophilus* spp., e.g. *Haemophilus influenzae; Chlamydia* spp., e.g. *Chlamydia trachomatis, Chlamydia pneumoniae, Chlamydia psittaci; Francisella fularensis; Bacillus* spp., e.g. *Bacillus anthracis; Clostridia* spp., e.g. *Clostridium botulinum; Yersinia* spp., e.g. *Yersinia pestis; Treponema* spp.; *Burkholderia* spp.; e.g. *Burkholderia mallei* and *B pseudomallei*, or the combination thereof. Preferably the infection is from one of the ESKAPE pathogens including *Enterococcus* spp., e.g. *Enterococcus faecalis; Staphylococcus* spp., e.g. *Staphylococcus aureus, Staphylococcus epidermidis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp., or the combination thereof. Also in one embodiment, the bacteria are selected from *Acidothermus cellulyticus, Actinomyces odontolyticus, Alkaliphilus metalliredigens, Alkaliphilus oremlandii, Arthrobacter aurescens, Bacillus amyloliquefaciens, Bacillus clausii, Bacillus halodurans, Bacillus licheniformis, Bacillus pumilus, Bacillus subtilis, Bifidobacterium adolescentis, Bifidiobacterium longum, Caldicellulosiruptor saccharolyticus, Carboxydothermus hydrogenoformans, Clostridium acetobutylicum, Clostridium beijerinckii, Clostridium botulinum, Clostridium cellulolyticum, Clostridium difficile, Clostridium kluyveri, Clostridium leptum, Clostridium novyi, Clostridium perfringens, Clostridium tetani, Clostridium thermocellum, Corynebacterium diphtheriae, Corynebacterium efficiens, Corynebacterium glutamicum, Corynebacterium jeikeium, Corynebacterium urealyticum, Desulfitobacterium hafniense, Desulfotomaculum reducens, Eubacterium ventriosum, Exiguobacterium sibiricum, Finegoldia magna, Geobacillus kaustophilus, Geobacillus thermodenitrificans, Janibacter* sp.*, Kineococcus radiotolerans, Lactobacillus fermentum, Listeria monocytogenes, Listeria innocua, Listeria welshimeri, Moorella thermoacetica, Mycobacterium avium, Mycobacterium bovis, Mycobacterium gilvum, Mycobacterium leprae, Mycobacterium paratuberculosis, Mycobacterium smegmatis, Mycobacterium tuberculosis, Mycobacterium ulcerans, Mycobacterium vanbaalenii, Nocardioides* sp.*, Nocardia farcinica, Oceanobacillus iheyensis, Pelotomaculum the rmopropionicum, Rhodococcus* sp.*, Saccharopolyspora erythraea*, coagulase-negative *Staphylococcus* species, *Staphylococcus aureus*, methicillin resistant *Staphylococcus aureus* (MRSA), *Staphylococcus epidermidis*, methicillin resistant *Staphylococcus epidermidis*, (MRSE), *Staphylococcus pseudintermedius, Staphylococcus intermedius, Staphylococcus delphini, Streptococcus agalactiae, Streptococcus gordonii, Streptococcus mitis, Streptococcus oralis, Streptococcus pneumoniae, Streptococcus sanguinis, Streptococcus suis, Streptomyces avermitilis, Streptomyces coelicolor, Thermoanaerobacter ethanolicus, Thermoanaerobacter tengcongensis*, or the combination thereof.

In another embodiment, the antibacterial composition of the present invention as described herein above is formulated into a topical pharmaceutical composition. The topical pharmaceutical composition comprises the antibacterial composition in various embodiments as defined herein above and one or more pharmaceutically acceptable carriers or excipients.

In another aspect, the present invention provides a topical pharmaceutical composition comprising as active agents 1) a composition A comprising polymyxin B and trimethoprim; and 2) one antibiotic agent that is a) rifamycin, or a rifamycin derivative selected from the group consisting of rifampicin (or rifampin), rifabutin, rifapentine, rifalazil and rifaximin or b) one selected from the group consisting of pefloxacin mesylate, sparfloxacin, sarafloxacin HCl, tobramycin, lomefloxacin, besifloxacin, danofloxacin mesylate, enrofloxacin, nadifloxacin and clinafloxacin and one or more pharmaceutically acceptable carriers or excipients, wherein the concentration of the composition A is from about 0.001 wt. % to about 8 wt. % per unit of the topical pharmaceutical composition and the concentration of the antibiotic agent is from about 0.001 wt. % to about 10 wt. % per unit of the topical pharmaceutical composition. In one embodiment, the concentration of the composition A is from about 0.015 wt. % to about 1 wt. % per unit of the topical pharmaceutical composition and the concentration of the antibiotic agent is from about 0.015 wt. % to about 2 wt. % per unit of the topical pharmaceutical composition. In one further embodiment, the weight ratio between the composition A and the antibiotic agent is from about 1:1000 to about 1000:1. In one embodiment, the weight ratio between the composition A and the antibiotic agent is from about 1:500 to about 500:1. In one embodiment, the weight ratio between the composition A and the antibiotic agent is from about 1:100 to about 100:1. In one embodiment, the weight ratio between the composition A and the antibiotic agent is from about 1:1 to about 50:1. In one embodiment, the weight ratio between the composition A and the antibiotic agent is from about 5:1 to about 25:1. In one embodiment, the weight ratio between the composition A and the antibiotic agent is about 1:1, about 1:10, about 1:15, about 1:20, about 1:30, about 1:40, about 1:50, about 1:60, about 1:70, about 1:80, about 1:90, about 1:100, about 1:125, about 1:150, about 1:175, about 1:200, about 1:250, about 1:300, about 1:350, about 1:400, about 1:450, about 1:500, about 1:550, about 1:600, about 1:650, about 1:700, about 1:750, about 1:800, about 1:850, about 1:900, about 1:950, or about 1:1000. In one embodiment, the weight ratio between the composition A and the antibiotic agent is about 2:1, about 3:1, about 4:1, about 5:1, about 8:1, about 10:1, about 15:1, about 20:1, about 25:1, about 30:1, about 40:1, about 50:1, about 60:1, about 70:1, about 80:1, about 90:1, about 100:1, about 125:1, about 150:1, about 175:1, about 190:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, or about 1000:1.

In one embodiment of the present invention, the composition A of the topical pharmaceutical composition consists of polymyxin B and trimethoprim. In one embodiment, the antibiotic agent of the topical pharmaceutical composition is rifampicin. In one embodiment, the composition A consists of polymyxin B and trimethoprim and the antibiotic agent is rifampicin. Also in another embodiment of the present invention, the antibacterial composition consists of as active agents polymyxin B, trimethoprim and rifampicin.

In one embodiment of the present invention, the composition A of the topical pharmaceutical composition comprises Polytrim. In one embodiment, the antibiotic agent of the topical pharmaceutical composition is rifampicin. In one embodiment, the composition A comprises Polytrim and the antibiotic agent is rifampicin. In one embodiment of the present invention, Polytrim and rifampicin are the only active agents.

In one embodiment, the antibacterial composition or the topical pharmaceutical composition as described herein is for treating ocular, otic, nasal, skin, or wound infection in a subject. In one embodiment, the infection is bacterial infection. In one embodiment, the bacterial ocular infection is bacterial keratitis, bacterial conjunctivitis, or bacterial endothalmitis. In further embodiment, the antibacterial composition or the topical pharmaceutical composition is for treating surface ocular bacterial infections, including acute bacterial conjunctivitis, and blepharoconjunctivitis, caused by susceptible strains of the following microorganisms: *Staphylococcus aureus, Staphylococcus epidermidis, Streptococcus pneumonia, Streptococcus viridans, Haemophilus influenza* and *Pseudomonas aeruginosa*, etc.

In one embodiment, the antibacterial composition or the topical pharmaceutical composition of the present invention may take the form of a cream, a lotion, an ointment, a hydrogel, a colloid, a gel, a foam, an oil, a milk, a suspension, a wipe, a sponge, a solution, an emulsion, a paste, a patch, a pladget, a swab, a dressing, a spray or a pad.

The topical composition of the present invention comprises one or more pharmaceutically acceptable carrier. Examples of the pharmaceutically acceptable carriers that are usable in the context of the present invention include carrier materials such as a solvent, a stabilizer, a solubilizer, a filler, a tonicity enhancing agent, a structure-forming agent, a suspending agent, a dispersing agent, a chelating agent, an emulsifying agent, an anti-foaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof.

Examples of solvents are water or purified water, alcohols (e.g., ethanol, benzyl alcohol), vegetable, marine and mineral oils, polyethylene glycols, propylene glycols, glycerol, and liquid polyalkylsiloxanes.

Inert diluents or fillers may be sucrose, sorbitol, sugar, mannitol, microcrystalline cellulose, starches, calcium carbonate, sodium chloride, lactose, calcium phosphate, calcium sulfate, or sodium phosphate.

Examples of buffering agents include citric acid, acetic acid, lactic acid, hydrogenophosphoric acid, diethylamine, sodium hydroxide and tromethane (i.e., tris(hydroxymethyl) aminomethane hydrochloride).

Suitable suspending agents are, for example, naturally occurring gums (e.g., acacia, arabic, xanthan, and tragacanth gum), celluloses (e.g., carboxymethyl-, hydroxyethyl-, hydroxypropyl-, and hydroxypropylmethyl-cellulose), alginates and chitosans.

Examples of dispersing or wetting agents are naturally occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives may be added to a topical composition of the invention to prevent microbial contamination that can affect the stability of the formulation and/or cause infection in the patient. Suitable examples of preservatives include parabens (such as methyl, ethyl, propyl, /p-hydroxybenzoate, butyl, isobutyl, and isopropylparaben), potassium sorbate, sorbic acid, benzoic acid, methyl benzoate, phenoxyethanol, bronopol, bronidox, MDM hydantoin, iodopropynyl butylcarbamate, benzalconium chloride, cetrimide, and benzylalcohol.

Examples of chelating agents include sodium EDTA and citric acid.

Examples of gel bases or viscosity-increasing agents are liquid paraffin, polyethylene, fatty oils, colloidal silica or aluminum, glycerol, propylene glycol, propylene carbonate, carboxyvinyl polymers, magnesium-aluminum silicates, hydrophilic polymers (such as, for example, starch or cellulose derivatives), water-swellable hydrocolloids, carragenans, hyaluronates, alginates, and acrylates.

Ointment bases suitable for use in the compositions of the present invention may be hydrophobic or hydrophilic, and include paraffin, lanolin, liquid polyalkylsiloxanes, cetanol, cetyl palmitate, vegetal oils, sorbitan esters of fatty acids, polyethylene glycols, and condensation products between sorbitan esters of fatty acids, ethylene oxide (e.g., polyoxyethylene sorbitan monooleate), polysorbates, white petrolatum and white wax.

Examples of humectants are ethanol, isopropanol glycerin, propylene glycol, sorbitol, lactic acid, and urea. Suitable emollients include cholesterol and glycerol.

Examples of skin protectants include vitamin E, allatoin, glycerin, zinc oxide, vitamins, and sunscreen agents.

Thickening agents are generally used to increase viscosity and improve bioadhesive properties of pharmaceutical or cosmetic compositions. Examples of thickening agents include, but are not limited to, celluloses, polyethylene glycol, polyethylene oxide, naturally occurring gums, gelatin, karaya, pectin, alginic acid, povidone, and Carbopol® polymers. Particularly interesting are thickening agents with thixotropic properties (i.e., agents whose viscosity is decreased by shaking or stirring). The presence of such an agent in a composition allows the viscosity of the composition to be reduced at the time of administration to facilitate its application to the skin and, to increase after application so that the composition remains at the site of administration.

Bioadhesive polymers are useful to hydrate the skin and enhance its permeability. Bioadhesive polymers can also function as thickening agents. Examples of bioadhesive polymers include, but are not limited to, pectin, alginic acid, chitosan, polysorbates, poly(ethyleneglycol), oligosaccharides and polysaccharides, cellulose esters and cellulose ethers, and modified cellulose polymers.

Permeation enhancing agents are vehicles containing specific agents that affect the delivery of active components through the skin. Permeation enhancing agents are generally divided into two classes: solvents and surface active compounds (amphiphilic molecules). Examples of solvent permeation enhancing agents include alcohols (e.g., ethyl alcohol, isopropyl alcohol), dimethyl formamide, dimethyl acetamide, dimethyl sulfoxide, 1-dodecylazocycloheptan-2-one, N-decyl-methylsulfoxide, lactic acid, N,N-diethyl-m-toluamide, N-methyl pyrrolidone, nonane, oleic acid, petrolatum, polyethylene glycol, propylene glycol, salicylic acid, urea, terpenes, and trichloroethanol. Surfactant permeation enhancing agents may be nonionic, amphoteric, cationic, or zwitterionic. Suitable nonioinic surfactants include poly(oxyethylene)-poly(oxypropylene) block copolymers, commercially known as poloxamers; ethoxylated hydrogenated castor oils; polysorbates, such as Tween 20 or Tween 80. Amphoteric surfactants include quaternized imidazole derivatives, cationic surfactants include cetypyridinium chloride, and zwitterionic surfactants include the betaines and sulfobetaines. Other examples of suitable permeation enhancers include pentadecalactone, 2-pyrrolidine, I-dodecal-azacycloheptane-2-one, calcium thioglycolate, hexanol, derivatives of 1,3-dioxanes (i.e., 1,3-dioxacyclohexanes) and 1,3-dioxalanes (i.e., 1,3-dioxacyclopentanes), 1-N-dodecyl-2-pyrrolidone-5-carboxylic acid, 2-pentyl-2-oxo-pyrrolidineacetic acid, 2-dodecyl-2-oxo-1-pyrrolidineacetic acid, and 1-azacycloheptan-2-one-2-dodecy lacetic acid among others.

In one embodiment, the topical pharmaceutical composition of the present invention is a topical ophthalmic pharmaceutical composition preferably in the form of a solution or suspension, an emulsion, an ointment, a cream, a gel, or a sustained release vehicle, such as an ocular insert.

In one example, the topical ophthalmic pharmaceutical composition of the present invention is a sterile liquid or gel, such as a solution or suspension, contained within a multi-use or single-use eye drop dispensing bottle or vial. In a specific example, the ophthalmic pharmaceutical composition is provided as a sterile liquid comprising from about 0.0015 to about 10.0 wt. % of the antibacterial composition described herein contained within a multi-use eye drop dispensing bottle or vial. Typically the eye drop formulation comprises an aqueous buffered saline solution such as phosphate or borate buffered saline from about pH 4 to about 8, typically from about pH 7.0 to about 8.0, and more typically from about pH 7.2 to about pH 7.4. The osmolality of the formulation is typically in the range of about 200, 250, or 270 mOsm/kg up to about 310, 350, or 400 mOsm/kg. A liquid formulation packaged in a multi-use eye drop dispensing bottle may contain an added preservative, such as benzalkonium chloride. However, in some examples, the ophthalmic composition may be preservative-free. As used herein, "preservative-free" means that the composition comprises no preservative agent in addition to the antibacterial composition.

The ophthalmic pharmaceutical composition when formulated as a liquid, such as a solution or a suspension for dispensing by eye dropper, may contain an excipient that extends the period of time that a dose of the composition remains in contact with the cornea. For example, the excipient may be a viscosity-increasing agent and/or a mucoadhesive agent. Examples of such excipients include high molecular weight hydrophilic polymers including, but not limited to, polyvinyl alcohol, polyethylene glycol, carbomers, polycarbophil, polyoxyethlene-polyoxypropylene block copolymers (e.g. Poloxamer 407), cellulose derivatives (e.g. hydroxypropyl cellulose, hydroxypropyl methyl cellulose, carboxymethyl cellulose, and hydroxyethyl cellulose), natural polysaccharides (e.g. hyaluronic acid, dextran, chondroitin sulfate, gellan gum, xanthan gum, guar gum, trehalose, and tamarind seed polysaccharide). Additional mucoadhesive polymers are described in the literature (see e.g. Yadav et al. J. Chem. Pharm. Res., 2010, 2(5):418-432, incorporated herein by reference). Any combination of two or more of the foregoing polymers may be included in composition. As used herein, a high molecular weight polymer has a molecular weight of at least 100,000 daltons. In another example, the composition comprises a cyclodextrin (e.g. 2-hydroxypropyl-beta-cyclodextrin). In one example, the composition is formulated as a sustained release liquid. For example, the composition may be in the form of an ophthalmic suspension comprising mucoadhesive microspheres which sustain release of the antibacterial composition. The microspheres comprise a mucoadhesive polymer and the antibacterial composition. Methods of making mucoadhesive microspheres for ophthalmic suspensions are described in the literature (see e.g. Dandagi et al., Sci Pharm (2013) 81(1):259-280).

In another specific example, the ophthalmic pharmaceutical composition is formulated as unit dose ocular insert for placement in the eye's cul de sac. Methods of making ocular inserts are described in the literature (see e.g. U.S. Pat. Nos. 4,730,013, 7,749,970, and U.S. Patent Application Publication No. US2012/0215184, which are incorporated herein by reference). An ocular insert is a solid unit dosage form comprising of a biodegradable matrix containing the active agent. The matrix is typically made from a high molecular weight polymer or a combination of high molecular weight polymers, such as the aforementioned hydrophilic polymers and additional polymers disclosed in the aforementioned patent publications that describe ocular inserts. The ocular insert may additionally comprise a lubricant to enhance comfort. Upon placement in the eye, the ocular insert dissolves or erodes over a period of several hours to a day, and in some cases over several days.

In another aspect, the present invention provides a method of treating a bacterial infection in a subject comprising administering to the subject separately, simultaneously or sequentially a therapeutically effective amount of the antibacterial composition described herein throughout the specification. In one embodiment, the antibacterial composition is formulated into a topical pharmaceutical composition. In one embodiment, the topical pharmaceutical composition is a formulation for treating ocular, otic or nasal infection. In one embodiment, the bacterial infection is from Gram-positive or Gram-negative bacteria or the combination of both.

In one embodiment, the topical pharmaceutical composition is an ophthalmic formulation for treating bacterial ocular infection. Non-limiting examples of the bacterial ocular infection are bacterial keratitis, bacterial conjunctivitis, or bacterial endothalmitis. In one example, the ophthalmic formulation is for treating surface ocular bacterial infections, including acute bacterial conjunctivitis, and blepharoconjunctivitis, caused by susceptible strains of the following microorganisms: *Staphylococcus aureus, Staphylococcus epidermidis, Streptococcus pneumonia, Streptococcus viridans, Haemophilus influenza* and *Pseudomonas aeruginosa*, etc.

In one embodiment, the present invention provides a method of decolonizing a bacterial organism comprising contacting the bacterial organism separately, simultaneously or sequentially with the antibacterial composition described herein throughout the specification.

In one embodiment, the present invention provides a method of decolonizing a bacterial organism comprising contacting the bacterial organism separately, simultaneously or sequentially with the topical pharmaceutical composition described herein throughout the specification.

In one embodiment, the present invention provides a method of destroying or disrupting or inhibiting or reducing biofilm formation a bacterial organism comprising contacting the bacterial organism separately, simultaneously or sequentially with the antibacterial composition described herein throughout the specification.

In one embodiment, the present invention provides a method of destroying or disrupting or inhibiting or reducing biofilm formation a bacterial organism comprising contacting the bacterial organism separately, simultaneously or sequentially with the topical pharmaceutical composition described herein throughout the specification.

Preferably the bacterium is one selected from the ESKAPE pathogens including *Enterococcus* spp., e.g. *Enterococcus faecalis; Staphylococcus* spp., e.g. *Staphylococcus aureus, Staphylococcus epidermidis; Klebsiella* spp., e.g. *Klebsiella pneumoniae; Acinetobacter* spp., e.g. *Acinetobacter baumannii; Pseudomonas* spp., e.g. *Pseudomonas aeruginosa; Enterobacter* spp., or the combination thereof.

The combination therapy of the present invention may be performed alone or in conjunction with another therapy. For example, the combination therapy of the present invention may be used in conjunction with a disinfectant, antiseptic, antibiotic, or biocide on a surface such as medical devices and indwelling devices including stents, catheters, peritoneal dialysis tubing, draining devices, joint prostheses, dental implants and the like.

By way of examples below, the present invention provides a synergistic combination therapy comprising composition A comprising polymyxin B and trimethoprim and one antibiotic agent that can be administered for the treatment of a microbial colonized surface or infection. Reference is now made to the following examples, which together with the above descriptions illustrate some embodiments of the invention in a non-limiting manner.

EXAMPLES

In order to address the problems in treating bacterial infections, we set out to create an improved trimethoprim/polymixin B formulation that displays improved antimicrobial efficacy toward contemporary *S. aureus* and *P. aeruginosa* keratitis isolates. Accordingly, members of an 853 member FDA approved drug library were screened for compounds that have the ability to improve the antibacterial activity of Polytrim. Our results indicate the addition of rifamycin class of antibiotics (i.e. rifampicin) potentiate the antimicrobial properties of Polytrim, leading to a lower effective dose and more rapid bactericidal activity. From these perspectives combinations of Polytrim and rifamycins are expected to represent a valuable new therapeutic option for the treatment of ocular infections that overcomes fluoroquinolone resistance and is more rapid-acting than that of Polytrim alone.

Example 1

Materials and Methods
Bacterial Strains and Growth Conditions

Bacterial strains used in these studies include the conventional laboratory strains *Pseudomonas aeruginosa* PA01 and *Staphylococcus aureus* UAMS-1, both of which are antibiotic susceptible and capable of forming robust biofilms. See Gillaspy A F, Hickmon S G, Skinner R A, Thomas J R, Nelson C L, Smeltzer M S. Role of the accessory gene regulator (agr) in pathogenesis of staphylococcal osteomyelitis. *Infection and immunity* 1995; 63:3373-3380. Seven clinical keratitis isolates of *Pseudomonas aeruginosa*, were collected from the Flaum Eye Institute, Rochester N.Y. and 25 clinical isolates of *Staphylococcus aureus* from geographically distinct regions of the country where purchased from International Health Management Associates (IHMA; Schaumburg, Ill.). For experiments requiring planktonic cultures, the indicated organism was grown overnight in Luria-Bertani broth (LB; Franklin Lakes, N.J.), diluted 1:100 in fresh media, grown to early exponential phase ($OD_{600nm}$ of 0.18 or 0.4 for *S. aureus* and *P. aeruginosa*, respectively) and processed. Biofilms were established by inoculating individual wells of flat-bottom polystyrene plates (Falcon, Corning Life Sciences; Durham, N.C.) with overnight cultures of the indicated organism into 200 ul of fresh LB to a final concentration of $1 \times 10^7$ CFU $ml^{-1}$. Plates were placed in a 37° C.-humidified incubator for 72 hours to allow static biofilm formation. Non-adherent cells were aspirated and biofilms were washed twice with phosphate-buffered saline prior to each experiment.

Chemicals and Compound Libraries

Tobramycin, rifampicin, neomycin, ciprofloxacin, ampicillin, gentamycin, besifloxacin and ceftriaxone were purchased from Sigma Aldrich (St. Louis, Mo.). Compounds already in ophthalmologic solution (moxifloxacin, polymyxin B/trimethoprim), were obtained from the Flaum Eye Institute (Rochester, N.Y.). A Library of 853 FDA approved drugs was obtained from Selleck Chemical (Houston, Tex.)

*Pseudomonas aeruginosa* Clinical Isolate Characterization

A series of genotyping and biological assays were used as a preliminary means to evaluate the clonality of clinical *P. aeruginosa* isolates collected, as follows. Genomic DNA was purified from each isolate using Qiagen DNeasy kits (Hilden, Germany) and used as a template for polymerase chain reactions to detect the presence of the virulence factors exoS, exoY, exoU, exoT, and perV using previously published primers (Table 1). See Allewelt M, Coleman F T, Grout M, Priebe G P, Pier G B. Acquisition of expression of the *Pseudomonas aeruginosa* ExoU cytotoxin leads to increased bacterial virulence in a murine model of acute pneumonia and systemic spread. *Infection and immunity* 2000; 68:3998-4004, Lomholt J A, Poulsen K, Kilian M. Epidemic population structure of *Pseudomonas aeruginosa*: evidence for a clone that is pathogenic to the eye and that has a distinct combination of virulence factors. *Infection and immunity* 2001; 69, and Ledbetter E C, Mun J J, Kowbel D, Fleiszig S M. Pathogenic phenotype and genotype of *Pseudomonas aeruginosa* isolates from spontaneous canine ocular infections. *Investigative ophthalmology & visual science* 2009; 50. The antibiotic susceptibility profiles of each isolate toward moxifloxacin, ceftriaxone, ampicillin, neomycin, gentamycin, tobramycin and polymyxin B/trimethoprim was evaluated following minimum inhibitory concentration (MIC) guidelines. See Institute C. Performance Standards for Antimicrobial Susceptibility Testing: Twenty-fifth Informational Supplement. *Performance Standards for Antimicrobial Susceptibility Testing: Twenty-fifth Informational Supplement*. Each isolate's ability to form biofilms was quantified. To do so, wells of a polystyrene plate containing 72-hour established biofilms were washed with 0.8% NaCl to remove non adherent cells and stained with crystal violet. To quantify biofilm staining, plates were washed 3 times with $H_2O$, stain was suspended in 30% glacial acetic acid and the optical density ($OD_{600nm}$) of each well was determined using an automated plate reader, as previously described. See Jacobs A C, Blanchard C E, Catherman S C, Dunman P M, Murata Y. An ribonuclease T2 family protein modulates *Acinetobacter baumannii* abiotic surface colonization. *PloS one* 2014; 9.

Selleck Library Screening

Figure 4A:
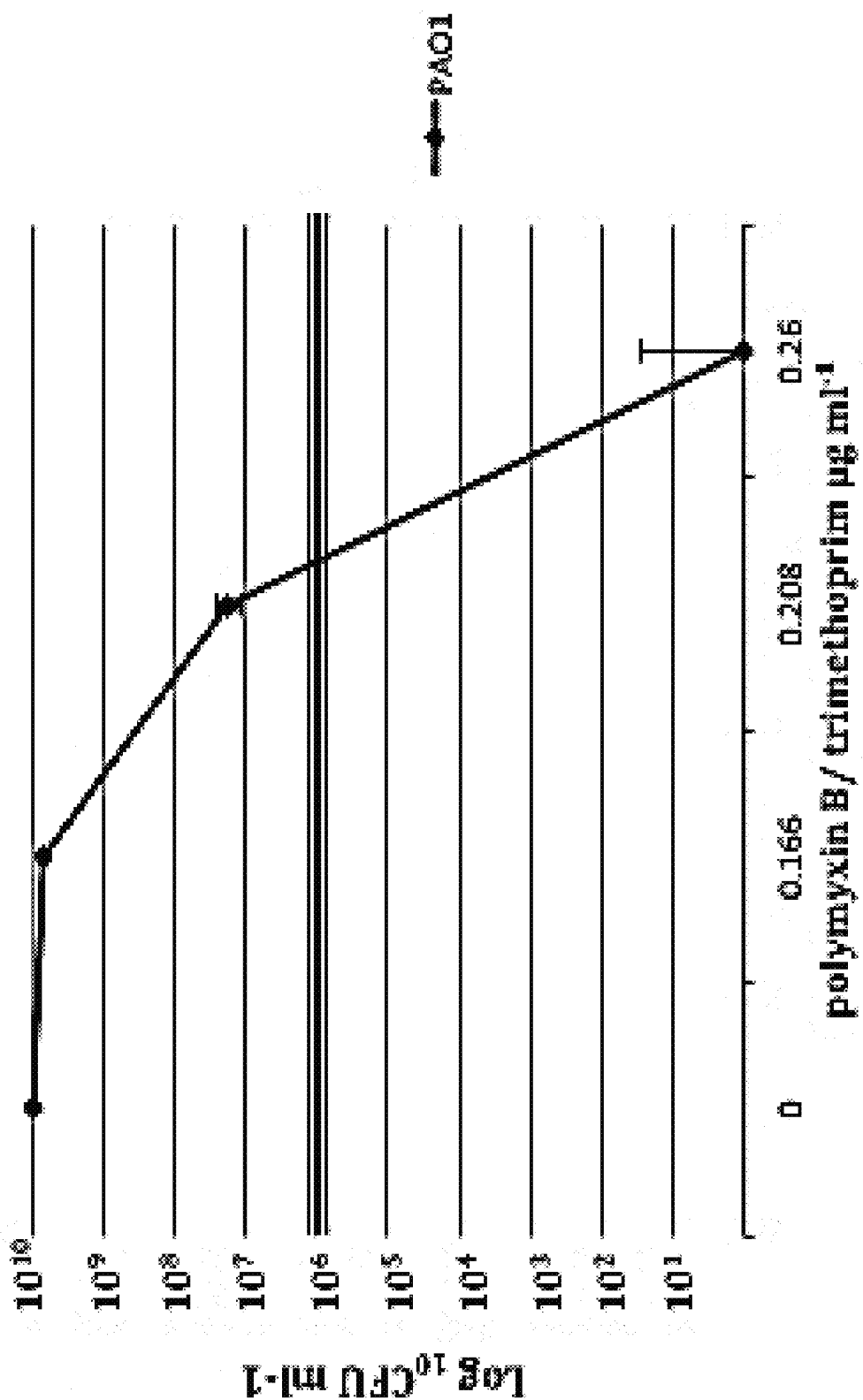
FIG. 4A and FIG. 4B, shows colony forming units of PAO1 (FIG. 4A) or UAMS-1 (FIG. 4B) in the presence of increasing concentrations of polymyxin B/trimethoprim. The concentration at which $10^6$ cells remained was considered sub-inhibitory and utilized in subsequent library screens.
Figure 4B:
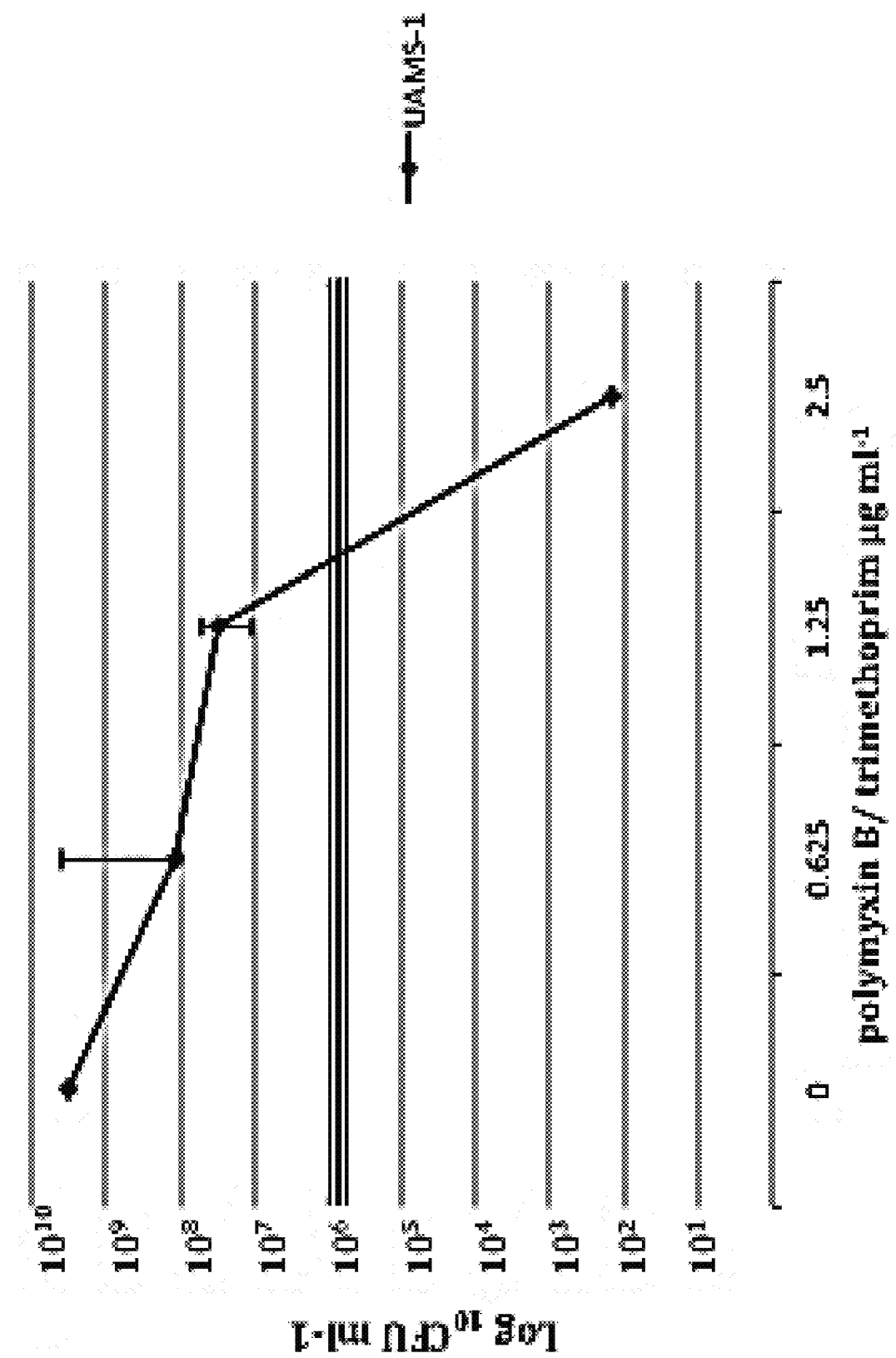

To identify agents that potentiate the antimicrobial activity of polymyxin B/trimethoprim we first determined the highest concentration of the polymyxin B/trimethoprim combination that allowed growth of *P. aeruginosa* strain PAO1 and *S. aureus* strain UAMS-1. To do so, standard MIC plate assays were performed in which $1\times10^5$ CFUs were added to each well of a microtiter plate in the presence of 2-fold increasing concentrations of polymyxin B/trimethoprim and incubated for 16 hr at 37° C. The MIC was identified as the drug concentration that did not exhibit growth, as measured by the unaided eye. To appreciate the more subtle effects of lower concentrations of drugs, aliquots (20 µl) were plated from wells representing each organism's 1×, 0.5×, 0.25×, and 0.125×MIC to determine the number of viable CFUs. The concentration of polymyxin B/trimethoprim that allowed survival of approximately $10^6$ CFU was selected for use in the screen as this represented a concentration with moderate antibacterial activity but that did not lead to a loss of growth phenotype following overnight incubation (FIG. 4).

For Selleck library screening, individual wells of 96-well microtiter plates containing 88 µl of fresh media were inoculated with approximately $10^5$ CFUs of *P. aeruginosa* strain PAO1 or *S. aureus* UAMS-1. Next, 2 µl of polymyxin B/trimethoprim was added to a final concentration of 0.2 µg $ml^{-1}$ or 1.25 µg $ml^{-1}$ for PA01 and UAMS-1, respectively. Library members were then added at either 5 µM or 50 µM final concentration. Plates were incubated at 37° C. for 16 hours and hits were identified as wells with no visible growth.

Fractional Inhibitory Concentration

In checkerboard format, *S. aureus* strain UAMS-1 or *P. aeruginosa* strain PA01 was added to individual wells of a microtiter plate. Rows of each plate were treated with

TABLE 1

Description of primers used in this study

| Gene (bp) | | Primers | Reference |
|---|---|---|---|
| exoU (428) | FWD | 5' GGG AAT ACTTTC CGG GAA GTT 3' (SEQ ID NO: 1) | Allewet et al., 2000, Infection and immunity, 68:3998-4004 |
| | REV | 5' CGA TCT CGC TGC TAA TGT GTT 3' (SEQ ID NO: 2) | |
| exoS (1352) | FWD | 5' ATC GCT TCA GCA GAG TCC GTC 3' (SEQ ID NO: 3) | Lomholt et al., 2001, Infection and immunity, 69:6284-95 |
| | REV | 5' CAG GCC AGA TCA AGG CCG CGC 3' (SEQ ID NO: 4) | |
| exoT (956) | FWD | 5' AAT CGC CGT CCA ACT GCA TGC G 3' (SEQ ID NO: 5) | Ledbetter et al., 2009, Investigative Ophthalmology and Visual Science, 50: 729-36 |
| | REV | 5' TGT TCG CCG AGG TAC TGC TC 3' (SEQ ID NO: 6) | |
| exoY (749) | FWD | 5' TCC AAG CTT ATG CGT ATC GAC GGT CA 3' (SEQ ID NO: 7) | Ledbetter et al., 2009, Investigative Ophthalmology and Visual Science, 50: 729-36 |
| | REV | 5' CGT ATC GAT CCG AGG GGG GTG TAT CT3' (SEQ ID NO: 8) | |
| pcrV (702) | FWD | 5' TCA CGA TGG AAG TCA GAA ACC 3' (SEQ ID NO: 9) | Stepinska et al., 2008, Microbial pathogenesis, 44:448-58 |
| | REV | 5' CCT TCT CGA GGG GGT ACT CA 3' (SEQ ID NO: 10) | | increasing concentrations of polymyxin B/trimethoprim (0 to 12.5 µg ml$^{-1}$), whereas each column was treated with increasing concentrations of rifampicin, tobramycin, or besifloxacin. Plates were incubated for 16 hr, at which time the concentration of each test agent that inhibited bacterial growth (alone) and at various combination concentrations was determined. The fractional inhibitory concentration (FIC) index was calculated using the formula: (Minimal inhibitory concentration (MIC) of drug A in combination/MIC of drug A alone)+(MIC of drug B in combination/MIC of drug B alone)=FIC. A synergistic interaction as defined as an FIC value of <0.5, an additive interaction was defined as an FIC value of 0.5 to 1.0, no interaction was defined as an FIC of 1 to 4, and an antagonistic interaction was defined as an FIC>4. See Odds F C. Synergy, antagonism, and what the chequerboard puts between them. *The Journal of antimicrobial chemotherapy* 2003; 52:1.

Biofilm Susceptibility

Biofilms were established as described above then treated with 100 µl of fresh media supplemented with 0.5×, 1×, 2×, 4× or 8× of the test agent's MIC toward planktonic PAO1 or UAMS-1 cells. After 24 hrs the remaining media and non-adherent cells were removed, biofilms were suspended in 0.8% NaCl and plated to quantify surviving bacteria. Susceptibilities of biofilms treated with a combination of compounds were determined in the same manner as above utilizing a ratio of 1:1 of each respective compound's planktonic MIC (i.e., 6.25 µg ml$^{-1}$ polymyxin B/trimethoprim and 15.6 µg ml$^{-1}$ rifampicin for PA01). Biofilms were treated in increasing increments ranging from 0 to 64×MIC.

Antimicrobial Kill Curves:

Overnight cultures of the indicated organism were used to inoculate (1:100 dilution) 100 ml of fresh media and grown to mid-exponential phase. Test compound(s) were added at 1×, 2×, or 4×MIC and culture incubation was allowed to continue. Aliquots were taken at 1, 2, 3, 4, and 24 hours, serial diluted and plated for colony forming units.

Resistance Measures

Spontaneous resistance to the indicated test agent(s) was measured for *P. aeruginosa* strain PA01 and *S. aureus* strain UAMS-1 using two liquid culture approaches. In the first, planktonic grown cells (1×10$^5$ CFUs were added to individual wells of a microtiter plate containing 100 µl Mueller Hinton medium supplemented with 1×MIC of rifampicin, 1×MIC polymyxin B/trimethoprim and 1×MIC in combination. Plates were incubated overnight at which time an aliquot was taken and plated to enumerate the number of viable colony forming units. For any test condition that exhibited putatively resistant viable cells, eight resultant colonies were randomly selected for repeat MIC testing as described above to establish whether they represented resistant isolates. As a secondary approach, 50 µl suspension from each treatment condition from above was transferred to a BacterioScan collection cuvette containing 1.95 ml of MH. Growth was measured using the BacterioScan s216Dx laser microbial growth monitor, with optical measurements taken every 3 minutes over 40 hours. Following 40 hours, samples were plated for to measure viable colony forming units and re-tested for drug susceptibility.

Example 2

Identification of Compounds that Improve the Antimicrobial Activity of Polymyxin B/Trimethoprim While ophthalmic solutions containing the antibiotics polymyxin B+trimethoprim display broad-spectrum antimicrobial activity and low resistance-associated clinical failure, the combination's therapeutic effectiveness has been limited, in part, by its relatively low potency toward certain bacterial species, slow kill-kinetics, and poor antibiofilm properties. To identify agents that could potentially improve the antimicrobial performance of polymyxin B/trimethoprim ophthalmic solutions members of an 853 member FDA approved drug library were initially screened for agents that confer antibacterial activity in the presence of an otherwise sub-inhibitory concentration of polymyxin B/trimethoprim. To do so, 10$^5$ CFUs of *S. aureus* strain UAMS-1 were inoculated in individual wells of a microtiter plate supplemented with 1.2 µg ml$^{-1}$ of polymyxin B/trimethoprim, (0.25×MIC). Library members were added at low (5 µM) or high (50 µM) concentrations and then scored for agents that inhibited growth following overnight incubation. Such agents were expected to represent compounds that display antimicrobial activity on their own and/or that potentiate the antimicrobial activity of polymyxin B/trimethoprim. In parallel the library was also screened at low and high concentration for agents that displayed a loss of growth phenotype toward *P. aeruginosa* PA01 cells inoculated in medium supplemented with 0.2 µg ml$^{-1}$ of polymyxin B/trimethoprim (0.5×MIC).

Screening results revealed that 153 library compounds exhibited a loss of *S. aureus* growth phenotype at 50 µM in the presence of 0.25×MIC polymyxin B/trimethoprim and of those, 75 also displayed antibacterial activity at 5 µM, suggesting that they represent the most potent anti-staphylococcal and/or potentiators of the antimicrobial performance of polymyxin B/trimethoprim. For *P. aeruginosa*, in the presence of 0.5×MIC polymyxin B/trimethoprim, a total of 63 compounds resulted in a loss of growth at 50 µM, 32 of which were also inhibited growth at 5 µM (Table 2).

TABLE 2

Positive screen results of polymyxin B/trimethoprim in combination with compounds within the FDA-approved Selleck Library at 50 µM and 5 µM against *S. aureus* UAMS-1 and *P. aeruginosa* PAO1.

| *S. aureus* UAMS-1[1] | | | *P. aeruginosa* PAO1[2] | |
|---|---|---|---|---|
| Azelnidipine | Erythromycin | Regorafenib | AMG-073 HCl | Levofloxacin |
| Azithromycin | Fenticonazole | Retapamulin | Amiodarone HCl | Lomefloxacin HCl |
| Balofloxacin | nitrate | Rifabutin | Azlocillin sodium salt | Miconazole |
| Besifloxacin HCl | Fleroxacin | Rifampicin | Aztreonam | Nadifloxacin |
| Bexarotene | Floxuridine | Rifapentine | Besifloxacin HCl | Pefloxacin |
| Biapenem | Gatifloxacin | Rifaximin | Cefoperazone | mesylate |
| Butoconazole | Gemcitabine | Roxithromycin | Ciprofloxacin | Pimecrolimus |
| nitrate | Granisetron HCl | Sarafloxacin HCl | Clinafloxacin | Ponatinib |
| Cefdinir | Idarubicin HCl | Sildenafil citrate | Crystal violet | Rifabutin |
| Cefditoren pivoxil | Lapatinib | Sitafloxacin | Danofloxacin | Rifampicin |
| Cefoperazone | Lincomycin HCl | hydrate | Doripenem Hydrate | Rifapentine |

TABLE 2-continued

Positive screen results of polymyxin B/trimethoprim in combination with compounds within the FDA-approved Selleck Library at 50 μM and 5 μM against *S. aureus* UAMS-1 and *P. aeruginosa* PAO1.

| S. aureus UAMS-1[1] | | | P. aeruginosa PAO1[2] | |
|---|---|---|---|---|
| Ciprofloxacin | Linezolid | Sorafenib | Enrofloxacin | Rifaximin |
| Clarithromycin | Lomefloxacin HCl | Sparfloxacin | Everolimus | Sarafloxacin HCl |
| Clinafloxacin | Marbofloxacin | Sulfamethizole | Gadodiamide | Sitafloxacin |
| Clindamycin HCl | Menadione | Sulfamethoxazole | Gatifloxacin | hydrate |
| Cloxacillin sodium | Meropenem | Sulfisoxazole | Granisetron HCl | Sparfloxacin |
| Crystal violet | Methacycline HCl | Sulphadimethoxine | Ivacaftor | Tobramycin |
| Danofloxacin | Miconazole | Tamoxifen Citrate | | |
| Dequalinium chloride | Moxifloxacin HCl | Tebipenem pivoxil | | |
| | Nadifloxacin | Teicoplanin | | |
| Doxycycline HCl | Nafcillin | Teniposide | | |
| Dronedarone HCl | Niclosamide | Tetracycline HCl | | |
| Econazole nitrate | Novobiocin sodium | Tioconazole | | |
| Eltrombopag | Pyrithione zinc | Tylosin tartrate | | |
| Enrofloxacin | | Vemurafenib | | |

[1]1.2 μg ml$^{-1}$ polymyxinB/trimethoprim;
[2]0.2 μg ml$^{-1}$ polymyxin B/trimethoprim.

In order to narrow the number of compounds for further study it was considered that the most therapeutically relevant polymyxin B/trimethoprim cocktail(s) would include agents that display potent activity toward both *S. aureus* and *P. aeruginosa*. A comparison of screen results for each organism revealed that 18 test agents exhibited activity against both *S. aureus* and *P. aeruginosa* at 5 μM and 50 μM. Moreover, 16 of these compounds were also previously reported to exhibit activity toward established *P. aeruginosa* biofilms, and *Acinetobacter baumannii*, which is recognized as a causative agent of keratitis. See Blanchard C, Brooks L, Ebsworth-Mojica K, et al. Zinc Pyrithione Improves the Antibacterial Activity of Silver Sulfadiazine Ointment. mSphere 2016; 1 and Colquhoun J M, Wozniak R A, Dunman P M. Clinically Relevant Growth Conditions Alter *Acinetobacter baumannii* Antibiotic Susceptibility and Promote Identification of Novel Antibacterial Agents. *PloS one* 2015; 10. These 16 compounds (Table 3) included 4 rifamycins (rifabutin, rifapentine, rifampicin, rifaximin), 2 quinolones (sarafloxacin and pefloxacin) and 8 fluoroquinolones (sparfloxacin, sitafloxacin, lomefloxacin, besifloxacin, danofloxacin, enrofloxacin, nadifloxacin and clinafloxacin). Two additional agents, levofloxacin and tobramycin, both of which demonstrated activity against *P. aeruginosa* at 5 μM and 50 μM but only activity at 50 μM against *S. aureus*, were included as levofloxacin is an FDA-approved fluoroquinolone for the treatment of corneal ulcers, and tobramycin, an aminoglycoside, is a commonly used fortified antibiotic utilized in the setting of fluoroquinolone treatment failure for bacterial keratitis; representatives of each class of antibiotic were selected for further investigation.

TABLE 3

Selected agents with activity against *S. aureus* and *P. aeruginosa* as well as performance in relevant assays.

| | S. aureus[1] | | P. aeruginosa | | P. aeruginosa biofilm[2] | A. baumanii[3] | | | AK |
|---|---|---|---|---|---|---|---|---|---|
| Drug | 5 μM | 50 μM | 5 μM | 50 μM | AK Signal | MH | Serum | Surfactant | Signal |
| Rifabutin | − | − | − | − | + | − | + | − | + |
| Rifapentine | − | − | − | − | + | − | + | − | + |
| Rifampicin | − | − | − | − | + | − | − | − | + |
| Rifaximin | − | − | − | − | + | − | − | − | + |
| Pefloxacin | − | − | − | − | + | − | + | − | + |
| Sparfloxacin | − | − | − | − | + | − | + | − | + |
| Levofloxacin | + | − | − | − | + | − | − | + | + |
| Sarafloxacin | − | − | − | − | + | − | + | − | + |
| Sitafloxacin | − | − | − | − | + | − | + | − | + |
| Tobramycin | + | − | − | − | + | − | + | − | +/− |
| Lomefloxacin | − | − | − | − | + | − | + | + | + |
| Besifloxacin | − | − | − | − | + | − | + | − | + |
| Danofloxacin | − | − | − | − | + | − | + | + | + |
| Enrofloxacin | − | − | − | − | + | − | + | − | + |
| Nadifloxacin | − | − | − | − | + | − | + | − | + |
| Clinafloxacin | − | − | − | − | + | − | + | − | + |

[1]Growth (+) or no growth (−) of *S. aureus* UAMS-1 in the presence of 1.2 μg ml$^{-1}$ polymyxin B/trimethoprim or *P. aeruginosa* PAO1 in the presence of 0.2 μg ml$^{-1}$ polymyxin B/trimethoprim at the indicated drug concentrations;
[2]Killing (+) of established biofilms as measured by the adenylate kinase reporter assay for bacterial cell death (Blanchard et al., 2016, mSphere, 1(5): e00194-16);
[3]Antimicrobial effects of each drug toward *A. baumanii* in Mueller Hinton (MH) broth, human serum, lung surfactant or established biofilm (Colquhoun et al., 2015, PLOS ONE, 10(11): e1043033).

Example 3

Rifampicin and Tobramycin Improve the Antimicrobial Activity of Polymyxin B/Trimethoprim In order to distinguish between agents with independent antibacterial activity from those that potentiate the antimicrobial activity of polymyxin B/trimethoprim, fractional inhibitory concentration (FIC) measures were performed in checkerboard format using rifampicin (rifamycin), tobramycin (aminoglycoside) and besifloxacin (fluoroquinolone) toward planktonic S. aureus and P. aeruginosa cultures. As shown in Table 4, antimicrobial susceptibility testing revealed that the MIC of P. aeruginosa strain PA01 toward polymyxin B/trimethoprim was 0.41 μg ml$^{-1}$, whereas the MICs for rifampicin, tobramycin and besifloxacin in isolation were 15.6 μg ml$^{-1}$, 0.48 μg ml$^{-1}$, and 1.56 μg ml$^{-1}$ respectively. The combination of rifampicin with polymyxin B/trimethoprim resulted in an additive effect against P. aeruginosa (FIC=0.637), suggesting that it potentiates the antimicrobial activity of polymyxin B/trimethoprim. Tobramycin (FIC=1.28) and besofloxacin (FIC=1) had neither additive nor antagonistic effects when in combination with polymyxin B/trimethoprim. Against S. aureus strain UAMS-1, the MIC of polymyxin B/trimethoprim was found to be 2 μg ml$^{-1}$, whereas the MICs for rifampicin, tobramycin and besifloxacin in isolation were found to be 0.01 μg ml$^{-1}$, 1.9 μg ml$^{-1}$, and 0.12 μg ml$^{-1}$ respectively (Table 4). In combination with polymyxin B/trimethoprim, rifampicin displayed a synergistic effect (FIC=0.469), and tobramycin had an additive effect (FIC=0.872), while besifloxacin showed no effect (FIC=1). Taken together, these results suggest that rifamycin such as rifampicin may improve the activity of polymyxin B/trimethoprim toward both P. aeruginosa and S. aureus, whereas tobramycin may improve polymyxin B/trimethoprim against S. aureus. To investigate if this improved activity extended to clinically relevant strains, fractional inhibitory concentration testing was extended to include a panel of contemporary S. aureus and P. aeruginosa clinical keratitis isolates.

TABLE 4

Minimum inhibitory concentration (MIC) and Fractional inhibitory concentration (FIC) of polymyxin B/trimethoprim (PT), rifampicin, tobramycin and besifloxacin alone and in combination.

| Strain | Alone μg ml$^{-1}$ | | Combination μg ml$^{-1}$ | | FIC Index |
|---|---|---|---|---|---|
| | PT | Rifampicin | PT | Rifampicin | |
| P. aeruginosa | 0.41 | 15.6 | 0.21 | 1.9 | 0.637 |
| S. aureus | 2.1 | 0.01 | 0.67 | 0.0015 | 0.469 |
| | PT | Tobramycin | PT | Tobramycin | |
| P. aeruginosa | 0.41 | 0.48 | 0.32 | 0.12 | 1.28 |
| S. aureus | 2.1 | 1.9 | 1.3 | 0.48 | 0.872 |
| | PT | Besifloxacin | PT | Besifloxacin | |
| P. aeruginosa | 0.41 | 1.56 | 0.205 | 0.78 | 1 |
| S. aureus | 2.1 | 0.12 | 1.05 | 0.06 | 1 |

Example 4

Efficacy of Polymyxin B/Trimethoprim in Combination with Rifampicin or Tobramycin Against Clinical Ocular Isolates Seven P. aeruginosa ocular tissue isolates were collected from the University of Rochester Flaum Eye Institute and subjected to preliminary genotyping and phenotypic analysis to ensure the strain set's diversity. To do so, PCR was used to assess the presence or absence of the virulence factors, exoS, exoY, exoU, exoT, and perV and antibiotic susceptibility profiles were established for each strain (Table 5). Results revealed that while all strains contained exoY, exoT and perV, four strains also contained exoS (RW01, RW02, RW03, RW06) while one contained exoU (RW07). Two strains contained neither exoS nor exoU (RW04, RW05). Strains with similar virulence factor patterns displayed a variety of resistance patterns suggesting they were not clonal strains. A S. aureus ocular clinical isolate set representing diverse clinical infection sites from varied regions of the country was also obtained. Taken together, it was considered that this collection of P. aeruginosa and S. aureus strains would represent a contemporary exploratory ocular isolate collection to evaluate the spectrum of activity of polymyxin B/trimethoprim in the absence and presence of rifampicin or tobramycin.

TABLE 5

Characteristics of clinical P. aeruginosa ocular isolates

| Strain | Source | Virulence Factors | | | | | Minimum Inhibitory Concentration (μg ml$^{-1}$) | | | | | | |
|---|---|---|---|---|---|---|---|---|---|---|---|---|---|
| | | exoS | exoY | exoU | exoT | perV | PT | Moxifloxacin | Ceftriaxone | Ampicillin | Neomycin | Gentamycin | Tobramycin |
| RW01 | Cornea | + | + | − | + | + | 0.41 | 0.25 | 13 | 50 | 9.8 | 0.24 | 0.24 |
| RW02 | Cornea | + | + | − | + | + | 0.41 | 0.25 | 26 | 50 | 9.8 | 0.24 | 0.24 |
| RW03 | Cornea | + | + | − | + | + | 0.51 | 0.25 | 26 | 50 | 9.8 | 0.12 | 0.24 |
| RW04 | Conjunctiva | − | + | − | + | + | 0.32 | 0.25 | 26 | 50 | 19.6 | 0.48 | 0.48 |
| RW05 | Cornea | − | + | − | + | + | 0.32 | .125 | 13 | 100 | 1 | 0.48 | 0.48 |
| RW06 | Cornea | + | + | − | + | + | 0.32 | 0.5 | 52 | 100 | 9.8 | 0.48 | 0.24 |
| RW07 | Cornea | − | + | + | + | + | 0.32 | 0.125 | 26 | 50 | 1 | 0.24 | 0.24 |

As shown in Table 6, antimicrobial susceptibility testing revealed that the combination of polymyxin B/trimethoprim with rifampicin exhibited improved antimicrobial activity compared to either polymyxin B+trimethoprim or rifampicin in isolation for all S. aureus and P. aeruginosa clinical isolates evaluated. Against P. aeruginosa, the combination generated an average FIC index of 0.509 (±0.04) suggesting an additive antimicrobial effect. Likewise for S. aureus, the combination resulted in a FIC of 0.463 (±0.04) suggesting an additive/synergistic antimicrobial effect between rifampicin and polymyxin B/trimethoprim. The addition of tobramycin to polymyxin B/trimethoprim exhibited more modest effects with an average FIC index of 1.14 (±0.17) for P. aeruginosa and 0.936 (±0.37) for S. aureus isolates suggesting a mild additive effect toward the latter (Table 7). The fact that rifampicin and to a lesser extent tobramycin in combination with polymyxin B/trimethoprim displayed improved activity against a variety of S. aureus and P. aeruginosa clinical isolates with varied resistance profiles highlights these combinations' clinical potential for the treatment of keratitis.

TABLE 6

Fractional inhibitory concentration testing of polymyxin B/trimethoprim + rifampicin against clinical isolates

| | | Minimum Inhibitory Concentration Measures ($\mu g\ ml^{-1}$) | | | | |
|---|---|---|---|---|---|---|
| | | Alone | | Combination | | FIC |
| Species | Strain | PT | Rifampicin | PT | Rifampicin | Index |
| P. aeruginosa | PAO1 | 0.41 | 15.6 | 0.21 | 1.9 | 0.634 |
| | RW01 | 0.41 | 15.6 | 0.13 | 1.9 | 0.439 |
| | RW02 | 0.41 | 15.6 | 0.16 | 1.9 | 0.512 |
| | RW03 | 0.51 | 15.6 | 0.16 | 3.9 | 0.564 |
| | RW04 | 0.32 | 15.6 | 0.13 | 1.9 | 0.528 |
| | RW05 | 0.32 | 31.25 | 0.13 | 1.9 | 0.467 |
| | RW06 | 0.32 | 15.6 | 0.13 | 1.9 | 0.528 |
| | RW07 | 0.32 | 15.6 | 0.13 | 1.9 | 0.528 |
| S. aureus | UAMS-1 | 2.1 | 0.01 | 0.67 | 0.0015 | 0.469 |
| | 1110936 | 1.6 | 0.05 | 0.67 | 0.0035 | 0.489 |
| | 1111063 | 2.1 | 0.1 | 0.67 | 0.0076 | 0.395 |
| | 1071788 | 1.6 | 0.01 | 0.67 | 0.0015 | 0.569 |
| | 1103430 | 2.1 | 0.01 | 0.67 | 0.0015 | 0.469 |
| | 1094094 | 2.1 | 0.01 | 0.67 | 0.0015 | 0.469 |
| | 1094140 | 2.1 | 0.01 | 0.67 | 0.0015 | 0.469 |
| | 1094147 | 2.1 | 0.01 | 0.67 | 0.0015 | 0.469 |
| | 1094166 | 2.1 | 0.01 | 0.67 | 0.0015 | 0.469 |
| | 1094178 | 2.1 | 0.1 | 0 67 | 0.0076 | 0.395 |
| | 1144105 | 1.6 | 0.05 | 0.67 | 0.0035 | 0.489 |
| | 1097612 | 2.1 | 0.05 | 0.67 | 0.0035 | 0.389 |
| | 1097630 | 2.1 | 0.01 | 0.67 | 0.0015 | 0.469 |
| | 1122181 | 2.1 | 0.01 | 0.67 | 0.0015 | 0.469 |
| | 1122187 | 2.1 | 0.05 | 0.67 | 0.0035 | 0.389 |
| | 1122190 | 1.6 | 0.05 | 0.67 | 0.0035 | 0.489 |
| | 1122197 | 2.1 | 0.01 | 0.67 | 0.0015 | 0.469 |
| | 1132822 | 2.1 | 0.01 | 0.67 | 0.0015 | 0.469 |
| | 1101442 | 1.6 | 0.05 | 0.67 | 0.0035 | 0.489 |
| | 1142776 | 2.1 | 0.01 | 0.67 | 0.0015 | 0.469 |
| | 1125120 | 2.1 | 0.05 | 0.67 | 0.0076 | 0.471 |

TABLE 7

Fractional inhibitory concentration testing of polymyxin B/trimethoprim + tobramycin against clinical isolates.

| | | Minimum Inhibitory Concentration Measures ($\mu g\ ml^{-1}$) | | | | |
|---|---|---|---|---|---|---|
| | | Alone | | Combination | | FIC |
| Species | Strain | PT | Tobramycin | PT | Tobramycin | Index |
| P. aeruginosa | PAO1 | 0.41 | 0.48 | 0.32 | 0.24 | 1.28 |
| | RW01 | 0.41 | 0.24 | 0.32 | 0.12 | 1.28 |
| | RW02 | 0.41 | 0.24 | 0.24 | 0.06 | 0.835 |
| | RW03 | 0.51 | 0.24 | 0.32 | 0.12 | 1.13 |
| | RW04 | 0.32 | 0.48 | 0.24 | 0.12 | 1.00 |
| | RW05 | 0.32 | 0.48 | 0.24 | 0.24 | 1.25 |
| | RW06 | 0.32 | 0.24 | 0.24 | 0.12 | 1.25 |
| | RW07 | 0.32 | 0.24 | 0.24 | 0.12 | 1.25 |
| S. aureus | UAMS-1 | 2.1 | 1.9 | 1.3 | 0.48 | 0.872 |
| | 1110936 | 1.6 | 1.9 | 0.67 | 0.48 | 0.671 |
| | 1111063 | 2.1 | 7.8 | 1.3 | 3.9 | 1.12 |
| | 1071788 | 1.6 | 0.97 | 0.67 | 0.48 | 0.914 |
| | 1103430 | 2.1 | 1.9 | 0.67 | 0.48 | 0.572 |
| | 1094094 | 2.1 | 3.9 | 0.67 | 3.9 | 1.32 |
| | 1094140 | 2.1 | 7.8 | 1.3 | 1.9 | 0.863 |
| | 1094147 | 2.1 | 7.8 | 0.67 | 3.9 | 0.819 |
| | 1094166 | 2.1 | 1.9 | 0.67 | 0.48 | 0.572 |
| | 1094178 | 2.1 | 7.8 | 1.6 | 7.8 | 1.76 |
| | 1144105 | 1.6 | 1.9 | 0.67 | 0.48 | 0.671 |
| | 1097612 | 2.1 | 15.6 | 1.3 | 3.9 | 0.869 |
| | 1097630 | 2.1 | 7.8 | 1.3 | 3.9 | 1.12 |
| | 1122181 | 2.1 | 7.8 | 1.3 | 3.9 | 1.12 |
| | 1122187 | 2.1 | 1.9 | 0.67 | 0.48 | 0.572 |
| | 1122190 | 1.6 | 7.8 | 1.3 | 3.9 | 1.31 |
| | 1122197 | 2.1 | 1.9 | 0.67 | 0.48 | 0.572 |
| | 1132822 | 2.1 | 3.9 | 1.3 | 0.97 | 0.868 |
| | 1101442 | 1.6 | 3.9 | 0.67 | 0.97 | 0.667 |
| | 1142776 | 2.1 | 1.9 | 0.67 | 0.48 | 0.572 |
| | 1125120 | 2.1 | 15.6 | 1.6 | 15.6 | 1.76 |

Example 5

Antimicrobial Effects of Polymyxin B/Trimethoprim in Combination with Rifampicin or Tobramycin Against Established Biofilms Given the propensity for both S. aureus and P. aeruginosa to form robust biofilms and the likely role of biofilms in potentiating corneal disease, the efficacy of polymyxin B/trimethoprim+either rifampicin or tobramycin was evaluated toward biofilms formed by each organism and compared to moxifloxacin, the current mainstay of keratitis treatment. As shown in FIG. 1A, treatment of established P. aeruginosa strain PAO1 biofilms with polymyxin B/trimethoprim (alone) exhibited mild anti-biofilm activity, resulting in a 2-log reduction in CFUs/ml at 32× the strain's planktonic polymyxin+trimethoprim MIC (0.41 $\mu g\ ml^{-1}$). Treatment of established P. aeruginosa biofilms with rifampicin (alone) or tobramycin (alone) produced similar dose-dependent responses each with a 5-log reduction in CFU at a concentration 32×MIC. The combination of, tobramycin+polymyxin B/trimethoprim performed slightly worse than tobramycin (alone) at concentrations between 2-4×MIC, but was equipotent to tobramycin (alone) at higher concentrations, resulting in a 5 log reduction in biofilm associated CFU at 32×MIC. Rifampicin+polymyxin B/trimethoprim outperformed rifampicin, tobramycin or polymyxin B/trimethoprim in a dose-dependent manner starting at 2×MIC, resulting in a maximum of 6-log reduction in CFU at 32×MIC. In comparison to moxifloxacin, rifampicin+polymyxin B/trimethoprim achieved a similar maximum log reduction at 32×MIC, however moxifloxacin did demonstrate improved anti-biofilm activity between 4×-16×MIC.

Antimicrobial testing of established *S. aureus* biofilms revealed that neither tobramycin, polymyxin B/trimethoprim nor their combination displayed significant activity against biofilm-associated cells at any concentration tested. Conversely, rifampicin (alone) displayed a dose-dependent reduction in biofilm-associated cells, resulting in a maximal reduction of a 4-log reduction in CFU at 32×MIC. Moxifloxacin demonstrated a similar dose response as rifampicin, achieving a 4 log reduction in CFU at 32×MIC. However, the combination of polymyxin B/trimethoprim and rifampicin demonstrated the most potent anti-biofilm activity, with significant antimicrobial activity observed at 2×MIC and a maximal 6-log reduction in CFU at 32×MIC. Taken together, these results indicate that the combinations of polymyxin B/trimethoprim containing rifampicin, and to a lesser extent tobramycin, display more potent antimicrobial activity against established *P. aeruginosa* and *S. aureus* biofilm-associated cells in comparison to the activity of these compounds tested individually. Moreover, this combination performs similarly to the common therapeutic moxifloxacin against *P. aeruginosa* biofilms and outperforms moxifloxacin against established *S. aureus* biofilms suggesting this combination could be efficacious and potentially superior in the treatment of ocular infections.

Example 6

Bactericidal Activity of Polymyxin B/Trimethoprim in Combination with Rifampicin The effectiveness of polymyxin B/trimethoprim when combined with rifampicin, and to a lesser extent tobramycin, toward established biofilms suggested these combinations exhibit improved bactericidal activity in comparison to each individually. To investigate the bactericidal effects of the combinations in more detail, standard kill-curve studies were performed using planktonic *S. aureus* and *P. aeruginosa* cells and compared to moxifloxacin. To do so, each organism was grown to early exponential phase, at which point cultures were treated with 2× the strain's MIC of rifampicin, tobramycin and polymyxin B/trimethoprim either alone or in combination and the number of viable CFUs was measured by plating.

Figure 2A:
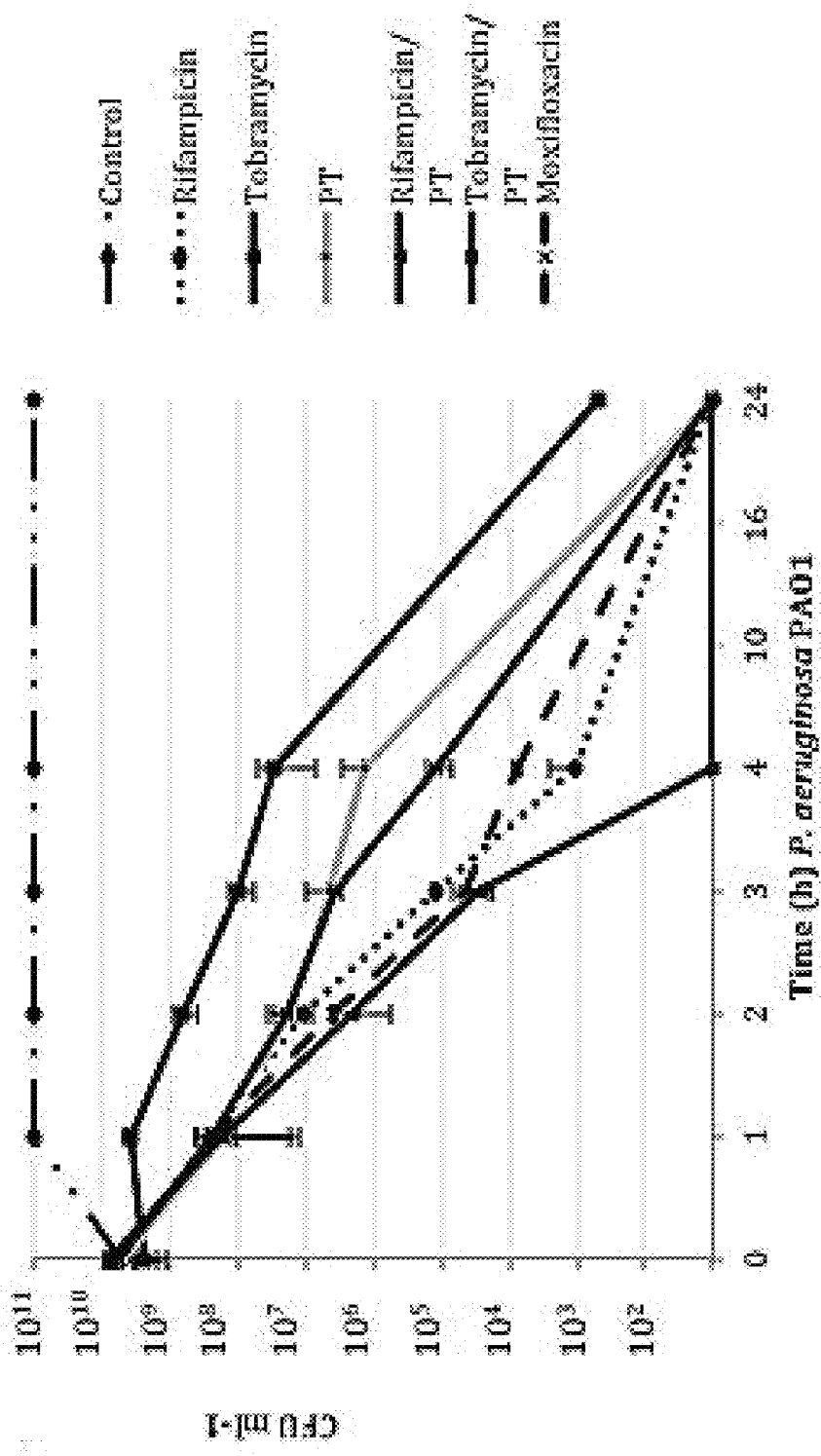
FIG. 2A and FIG. 2B, shows rate of killing of moxifloxacin, tobramycin, polymyxin B/trimethoprim, rifampicin, polymyxin B/trimethoprim+rifampicin, and polymyxin B/trimethoprim+tobramycin against *P. aeruginosa* PA01 (FIG. 2A) and *S. aureus* UAMS-1 (FIG. 2B).

As shown in FIG. 2A, *P. aeruginosa* kill curves revealed that tobramycin (alone) exhibited an initial modest 2-log reduction in CFU at hour 4 post-treatment that further increased to a maximal 7-log reduction in CFU at 24 hr challenge. Polymyxin B/trimethoprim (alone) resulted in a 3-log CFU reduction by hour 4 treatment and complete eradication of viable cells by hour 24. In combination, tobramycin+polymyxin B/trimethoprim treated *P. aeruginosa* cells behaved similarly to polymyxin B/trimethoprim (alone) between hours 1-3, and demonstrated slightly improved bactericidal activity at hour 4 post-treatment resulting in a 4-log reduction in CFU and complete eradication of cells by 24 hours. Rifampicin in isolation produced a 6-log CFU reduction by hour 4 with no viable cells at 24 hours. Moxifloxacin performed similarly to rifampicin between hours 1-3, however only demonstrated a 5-log CFU reduction at hour 4, followed by complete eradiation in 24 hours. However, there was notable improvement in bactericidal activity of polymyxin B/trimethoprim+rifampicin compared to either polymyxin B/trimethoprim or moxifloxacin monotherapy starting at 2 hours after treatment that resulted in complete eradication of viable cells by 4 hours.

Figure 2B:
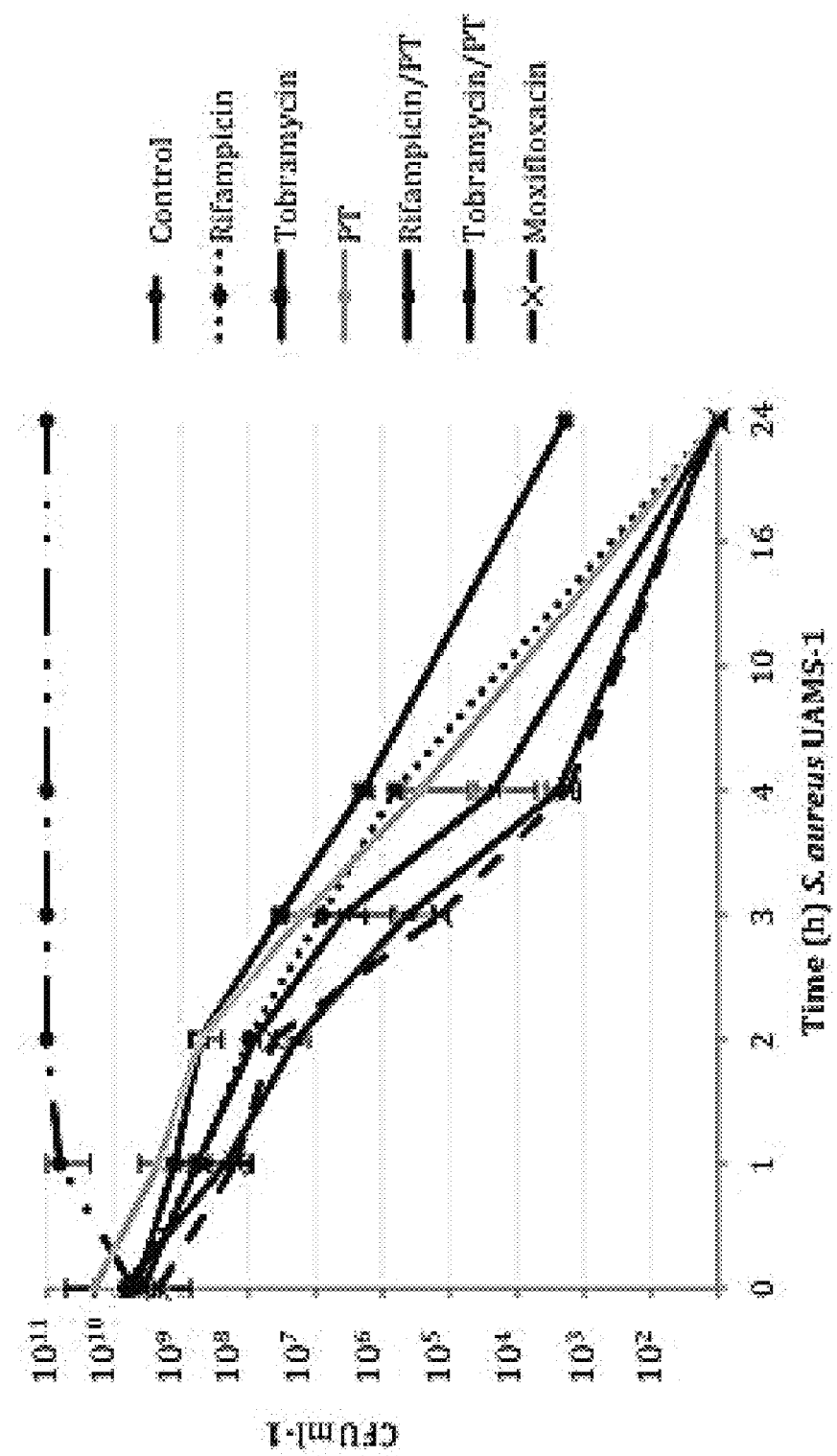

Against *S. aureus*, tobramycin, polymyxin B/trimethoprim and rifampicin produced similar kill curves between hours 1-4, resulting in a 3-4 log reduction at 4 hours post-treatment (FIG. 2B). At 24 hours, tobramycin (alone) resulted in a 6-log reduction in CFU, whereas both rifampicin and polymyxin B/trimethoprim resulted in eradication of viable cells. Tobramycin in combination with polymyxin B/trimethoprim demonstrated improved bactericidal activity by hour 4 with 5-log reduction in CFU and complete eradication by hour 24. Rifampicin in combination with polymyxin B/trimethoprim resulted in improved bactericidal activity emerging by hour 2 with a 6-log reduction in viable cells at hour 4 and no recoverable viable cells at hour 24. This activity was nearly identical to moxifloxacin at all time points. Taken together these results indicate improved bactericidal activity of rifampicin in combination with polymyxin B/trimethoprim against both *S. aureus* and *P. aeruginosa* that is either equivalent or superior to moxifloxacin.

Example 7

Improved Antimicrobial Resistance Profile of Polymyxin B/Trimethoprim+Rifampicin The spontaneous resistance frequency of *S. aureus* strain UAMS-1 and *P. aeruginosa* strain PAO1 towards rifampicin, polymyxin B/trimethoprim and their combination was evaluated using two methods. Using *P. aeruginosa* PAO1 or *S. aureus* UAMS-1, approximately $10^6$ planktonic cells were treated with either 1×MIC of rifampicin, polymyxin B/trimethoprim or the 1×MIC of each in combination for 20 hours after which the culture was plated to isolate individual colonies. To determine if these colonies represented untreated cells vs. resistant cells, 8 individual colonies from each treatment condition were randomly selected and tested for MICs. Both *S. aureus* and *P. aeruginosa* cells previously treated with rifampicin produced rifampicin resistance between 2-4× of the original MIC. Likewise for cells treated with polymyxin B/trimethoprim, resultant outgrowth contained resistant cells at 2-4× the original MIC. The combination of rifampicin and polymyxin B/trimethoprim did not result in any recoverable viable *S. aureus* or *P. aeruginosa* cells at 20 hours, and thus no resistant colonies were isolated (Data not shown).

Figure 3A:
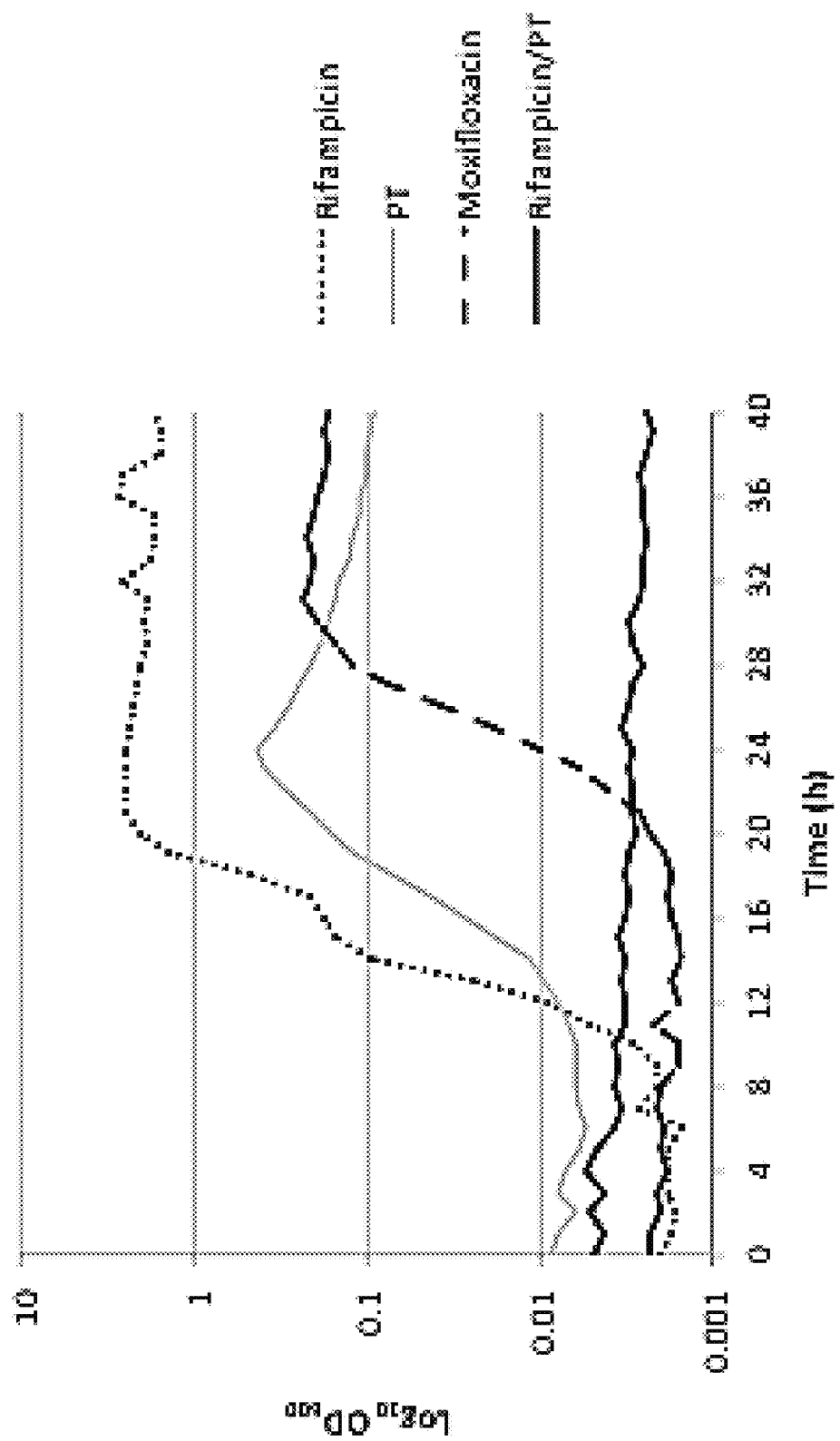
FIG. 3A and FIG. 3B, shows growth of resistant *P. aeruginosa* PAO1 cells (FIG. 3A) and *S. aureus* (FIG. 3B) after treatment with rifampicin, polymyxin B/trimethoprim, or their combination compared to moxifloxacin over 40 hours.

To further study the propensity to develop resistance among cultures treated with rifampicin, polymyxin B/trimethoprim or their combination, as well as moxifloxacin, growth of *S. aureus* or *P. aeruginosa* planktonic cultures in mid exponential phase were followed for 40 hours following treatment at 1×MIC of each compound individually and in combination. Using an automated laser microbial growth monitor, the optical profiles of these cultures were measured continuously over time. As shown in FIG. 3a, *P. aeruginosa* cultures treated with rifampicin (alone) or polymyxin B/trimethoprim (alone) demonstrated minimal growth for the first 10-12 hours. However, subsequently, cells under each of these conditions demonstrated exponential growth suggesting the development of resistance factors. Moxifloxacin treated cells did not show growth until approximately 22 hours of incubation, after which they also entered into exponential growth. The combination of rifampicin+polymyxin B/trimethoprim, however, did not show any growth throughout 40 hours, suggesting this combination has a much lower propensity to develop resistance. To confirm that recovered cells from rifampicin-only, polymyxin B/trimethoprim-only or moxifloxacin treated cultures demonstrated resistance, these cultures were subsequently retested for MICs. Again 8 colonies were selected at random from each treatment group. Cells that grew from cultures treated with rifampicin demonstrated resistance at 2-8×MIC. In the polymyxin B/trimethoprim treatment group, 7/8 colonies demonstrated resistance at 2×MIC while 1 colony was found to be sensitive suggesting that growth seen after treatment represents a mixture of resistant and non-treated cells. Moxifloxacin treated cells demonstrated resistance at 2×MIC. There were no recoverable cells from the rifampicin+polymyxin B/trimethoprim treated cultures.

Figure 3B:
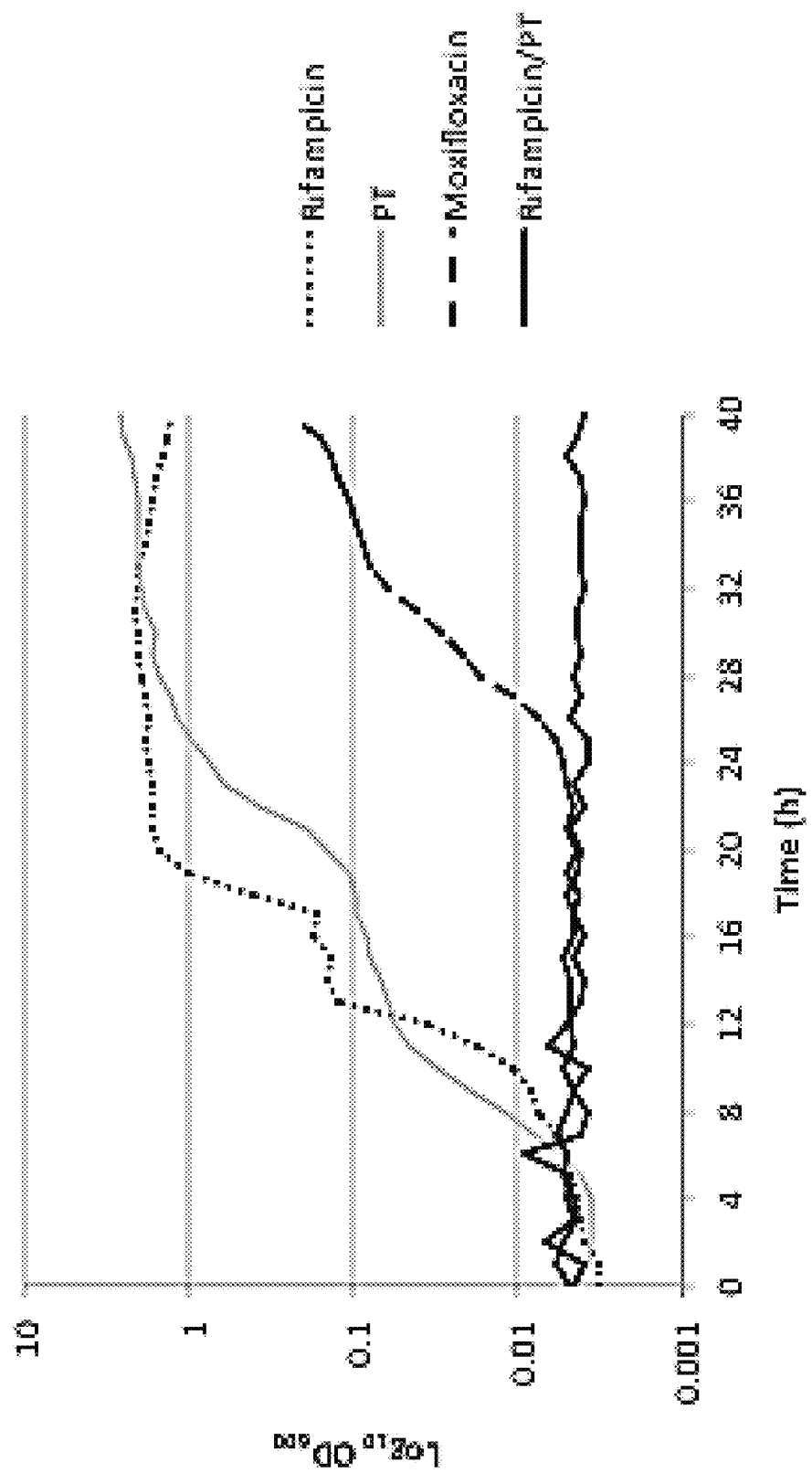

With respect to S. aureus, rifampicin-only and polymyxin B/trimethoprim-only treated cells demonstrated outgrowth starting at 8 hours, while moxifloxacin treated cells demonstrated growth starting at 26 hours (FIG. 3B). However, cells treated with the combination of rifampicin and polymyxin B/trimethoprim did not demonstrate any growth during the 40 hour time period. Again, cultures were retested for resistance and demonstrated an increase of 2-4×MIC for each compound tested. Thus, taken together, moxifloxacin, polymyxin B/trimethoprim and rifampicin in isolation all demonstrated rapid development of resistant colonies in both S. aureus and P. aeruginosa. However, no resistant colonies could be identified after treatment with the combination of polymyxin B/trimethoprim+rifampicin indicating an improved resistance profile.

CONCLUSION

Fluoroquinolones have been successfully used for broad spectrum empiric infectious keratitis treatment, yet the emergence of corresponding resistance has led to clinical failure and highlighted the need for new therapeutic alternatives. See Bertino J S. Impact of antibiotic resistance in the management of ocular infections: the role of current and future antibiotics. *Clinical ophthalmology* (Auckland, NZ) 2009; 3:507-521 and Collier S A, Gronostaj M P, MacGurn A K, et al. Estimated burden of keratitis—United States, 2010. *MMWR Morbidity and mortality weekly report* 2014; 63: 1027-1030. While specialty compounded antibiotics such as vancomycin or tobramycin are available in some academic centers to circumvent emerging resistance, there are limited alternative commercial options for treatment.

In that regard, polymyxin B/trimethoprim is currently available as a topical ophthalmic antibiotic combination for the treatment of bacterial conjunctivitis. See Granet D B, Dorfman M, Stroman D, Cockrum P. A multicenter comparison of polymyxin B sulfate/trimethoprim ophthalmic solution and moxifloxacin in the speed of clinical efficacy for the treatment of bacterial conjunctivitis. *Journal of pediatric ophthalmology and strabismus* 2008; 45:340-349. Despite some inherent limitations to this drug, namely weaker ocular tissue penetration, slower kill rate and limited antibiofilm activity, its resistance rate is more favorable compared to fluoroquinolones suggesting this combination may provide a platform for improvement, which was a goal of this study. The focus in the described studies was limited to P. aeruginosa and S. aureus, two organisms that account for the vast majority of bacterial keratitis infections.

The results presented suggest that the addition of rifamycin such as rifampicin to polymyxin B/trimethoprim suspensions results in an additive antimicrobial effect against both laboratory and clinical isolates of P. aeruginosa and a synergistic effect toward S. aureus strains, thereby reducing the effective concentration needed to result in an effective dose. Moreover, the improved antimicrobial performance of the combination of rifampicin+polymyxin B/trimethoprim was observed toward established biofilms formed by either S. aureus or P. aeruginosa.

The formation of biofilms in infection poses particular treatment challenges as physiologic and metabolic changes can result in cells recalcitrant to traditional antimicrobial therapy. While the role of biofilms has not been explicitly established in active bacterial keratitis, these complex structures are widely accepted to be important in a variety of ocular infections. Additionally, both S. aureus and P. aeruginosa readily form biofilms on contact lenses. In the United States and other developed countries, contact lens use remains the primary risk factor for developing keratitis. Nearly 30 million people in the U. S. wear contact lenses and infectious keratitis will affect 1 out of every 500 contact lens users per year, leading to nearly 1 million doctor visits at a cost of $175 million to the US health care system annually[35]. Thus antibiotics with potent anti-biofilm activity may be of particular importance in this group of patients. Importantly polymyxin B/trimethoprim+rifampicin demonstrated improved anti-biofilm activity against S. aureus and equivalent activity against P. aeruginosa when in comparison to moxifloxacin, a fourth generation fluoroquinolone that is commonly utilized in the treatment of bacterial keratitis.

The combination of rifampicin and polymyxin B/trimethoprim also demonstrated a lower propensity to develop resistance compared to either compound in isolation as well as moxifloxacin. This may be in part due to the fact that rifampicin, polymyxin B and trimethoprim all have unique modes of action; rifampicin inhibits bacterial DNA transcription by binding to RNA polymerase, trimethoprim inhibits bacterial DNA synthesis through the inhibition of dihydrofolate reductase and polymyxin B acts as a detergent to disrupt the outer and inner membranes of Gram-negative bacteria. Given these disparate modes of action, multiple mutations would be required to overcome each of these areas of inhibition. The simultaneous targeting of disparate pathways is a common strategy to overcome existing resistance in a variety of infections including HIV, malaria and tuberculosis. See Worthington R J, Melander C. Combination approaches to combat multidrug-resistant bacteria. *Trends in biotechnology* 2013; 31 and Fischbach M A. Combination therapies for combating antimicrobial resistance. *Current opinion in microbiology* 2011; 14. While there may be unforeseen effects of combination drugs with respect to toxicity, both rifampicin and polymyxin B/trimethoprim are currently FDA-approved drugs with favorable safety profiles thus their combination may provide a significant advantage for further drug development.

In summary, rifampicin+polymyxin B/trimethoprim may represent a novel antibiotic combination with broad spectrum antimicrobial activity, rapid bactericidal action, anti-biofilm activity and a reduced resistance frequency for the treatment of bacterial keratitis. By identifying a combination of previously FDA approved drugs for further study there is an increased potential for expedited development in an era of critical need for novel antimicrobial therapeutics.

What is claimed is:

1. An antibacterial composition comprising as active agents 1) a composition A comprising polymyxin B and trimethoprim; and 2) one antibiotic agent that is rifamycin, or a rifamycin derivative selected from the group consisting of rifampicin (or rifampin), rifabutin, rifapentine, rifalazil and rifaximin and one or more pharmaceutically acceptable carriers or excipients.

2. The antibacterial composition of claim 1, wherein the weight ratio between the composition A and the antibiotic agent is from about 1:1000 to about 1000:1.

3. The antibacterial composition of claim 2, wherein the weight ratio between the composition A and the antibiotic agent is from about 1:500 to about 500:1.

4. The antibacterial composition of claim 2, wherein the weight ratio between the composition A and the antibiotic agent is from about 1:100 to about 100:1.

5. The antibacterial composition of claim 2, wherein the weight ratio between the composition A and the antibiotic agent is about 1:1, about 1:10, about 1:15, about 1:20, about 1:30, about 1:40, about 1:50, about 1:60, about 1:70, about 1:80, about 1:90, about 1:100, about 1:125, about 1:150, about 1:175, about 1:200, about 1:250, about 1:300, about 1:350, about 1:400, about 1:450, about 1:500, about 1:550, about 1:600, about 1:650, about 1:700, about 1:750, about 1:800, about 1:850, about 1:900, about 1:950, about 1:1000, about 2:1, about 3:1, about 4:1, about 5:1, about 8:1, about 10:1, about 15:1, about 20:1, about 25:1, about 30:1, about 40:1, about 50:1, about 60:1, about 70:1, about 80:1, about 90:1, about 100:1, about 125:1, about 150:1, about 175:1, about 190:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, or about 1000:1.

6. The antibacterial composition of claim 1, wherein the antibiotic agent is rifampicin.

7. The antibacterial composition of claim 1, wherein the composition A consists of polymyxin B and trimethoprim and the antibiotic agent is rifampicin.

8. The antibacterial composition of claim 1, wherein the antibiotic agent is rifampicin.

9. The antibacterial composition of claim 8, wherein polymyxin B, trimethoprim and rifampicin are the only active agents.

10. The antibacterial composition claim 1, wherein the total concentration of the composition A and the antibiotic agent is from about 1 wt. % to about 50 wt. %.

11. A topical pharmaceutical composition comprising as active agents 1) a composition A comprising polymyxin B and trimethoprim; and 2) an antibiotic agent that is rifamycin, or a rifamycin derivative selected from the group consisting of rifampicin (or rifampin), rifabutin, rifapentine, rifalazil and rifaximin and one or more pharmaceutically acceptable carriers or excipients.

12. The topical pharmaceutical composition of claim 11, wherein the weight ratio between the composition A and the antibiotic agent is from about 1:1000 to about 1000:1.

13. The topical pharmaceutical composition of claim 12, wherein the weight ratio between the composition A and the antibiotic agent is from 1:500 to about 500:1.

14. The topical pharmaceutical composition of claim 12, wherein the weight ratio between the composition A and the antibiotic agent is from 1:100 to about 100:1.

15. The topical pharmaceutical composition of claim 12, wherein the weight ratio between the composition A and the antibiotic agent is about 1:1, about 1:10, about 1:15, about 1:20, about 1:30, about 1:40, about 1:50, about 1:60, about 1:70, about 1:80, about 1:90, about 1:100, about 1:125, about 1:150, about 1:175, about 1:200, about 1:250, about 1:300, about 1:350, about 1:400, about 1:450, about 1:500, about 1:550, about 1:600, about 1:650, about 1:700, about 1:750, about 1:800, about 1:850, about 1:900, about 1:950, about 1:1000, about 2:1, about 3:1, about 4:1, about 5:1, about 8:1, about 10:1, about 15:1, about 20:1, about 25:1, about 30:1, about 40:1, about 50:1, about 60:1, about 70:1, about 80:1, about 90:1, about 100:1, about 125:1, about 150:1, about 175:1, about 190:1, about 200:1, about 250:1, about 300:1, about 350:1, about 400:1, about 450:1, about 500:1, about 550:1, about 600:1, about 650:1, about 700:1, about 750:1, about 800:1, about 850:1, about 900:1, about 950:1, or about 1000:1.

16. The topical pharmaceutical composition of claim 11, wherein the antibiotic agent is rifampicin.

17. The topical pharmaceutical composition of claim 11, wherein the composition A consists of polymyxin B and trimethoprim and the antibiotic agent is rifampicin.

18. The topical pharmaceutical composition of claim 16, wherein polymyxin B and trimethoprim and rifampicin are the only active agents.

19. The topical pharmaceutical composition of claim 11, wherein the composition is for treating a bacterial ocular infection in a subject.

20. The topical pharmaceutical composition of claim 19, wherein the bacterial ocular infection is bacterial keratitis, bacterial conjunctivitis, or bacterial endothalmitis.

21. A topical pharmaceutical composition comprising as active agents 1) a composition A comprising polymyxin B and trimethoprim; and 2) an antibiotic agent that is rifamycin, or a rifamycin derivative selected from the group consisting of rifampicin (or rifampin), rifabutin, rifapentine, rifalazil and rifaximin and one or more pharmaceutically acceptable carriers or excipients, wherein the concentration of the composition A is from about 0.001 wt. % to about 8 wt. % per unit of the topical pharmaceutical composition and the concentration of the antibiotic agent is from about 0.001 wt. % to about 10 wt. % per unit of the topical pharmaceutical composition.

22. The topical pharmaceutical composition of claim 21, wherein the weight ratio between the composition A and the antibiotic agent is from about 1:1000 to about 1000:1.

23. The topical pharmaceutical composition of claim 21, wherein the antibiotic agent is rifampicin.

24. The topical pharmaceutical composition of any of claim 21, wherein the composition A consists of polymyxin B and trimethoprim and the antibiotic agent is rifampicin.

25. The topical pharmaceutical composition of claim 23, wherein polymyxin B, trimethoprim and rifampicin are the only active agents.

26. A method of treating a bacterial ocular infection in a subject comprising administering to the subject a therapeutically effective amount of the composition of claim 1.

27. The method of claim 26, wherein the bacterial ocular infection is a surface ocular bacterial infection is selected from the group consisting of acute bacterial conjunctivitis, and blepharoconjunctivitis, caused by at least one susceptible strain of *Staphylococcus aureus, Staphylococcus epidermidis, Streptococcus pneumonia, Streptococcus viridans, Haemophilus influenza* or *Pseudomonas aeruginosa*.

28. The method of claim 26, wherein the bacterial ocular infection is characterized with colonization or biofilm formation of a bacterium.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence

```
<220> FEATURE:
<223> OTHER INFORMATION: Chemically synthesized

<400> SEQUENCE: 1
gggaatactt tccgggaagt t                                              21

<210> SEQ ID NO 2
<211> LENGTH: 21
<212> TYPE: DNA
<213> ORGANISM: Artificial Sequence
<220> FEATURE:
<223> OTHER INFORMATION: Chemically synthesized

<400> SEQUENCE: 2
cgatctcgct gctaatgtgt t                                              21

<210> SEQ ID NO 3
<211> LENGTH: 21
<212> TYPE: DNA
<213> ORGANISM: Artificial Sequence
<220> FEATURE:
<223> OTHER INFORMATION: Chemically synthesized

<400> SEQUENCE: 3
atcgcttcag cagagtccgt c                                              21

<210> SEQ ID NO 4
<211> LENGTH: 21
<212> TYPE: DNA
<213> ORGANISM: Artificial Sequence
<220> FEATURE:
<223> OTHER INFORMATION: Chemically synthesized

<400> SEQUENCE: 4
caggccagat caaggccgcg c                                              21

<210> SEQ ID NO 5
<211> LENGTH: 22
<212> TYPE: DNA
<213> ORGANISM: Artificial Sequence
<220> FEATURE:
<223> OTHER INFORMATION: Chemically synthesized

<400> SEQUENCE: 5
aatcgccgtc caactgcatg cg                                             22

<210> SEQ ID NO 6
<211> LENGTH: 20
<212> TYPE: DNA
<213> ORGANISM: Artificial Sequence
<220> FEATURE:
<223> OTHER INFORMATION: Chemically synthesized

<400> SEQUENCE: 6
tgttcgccga ggtactgctc                                                20

<210> SEQ ID NO 7
<211> LENGTH: 26
<212> TYPE: DNA
<213> ORGANISM: Artificial Sequence
<220> FEATURE:
<223> OTHER INFORMATION: Chemically synthesized

<400> SEQUENCE: 7
tccaagctta tgcgtatcga cggtca                                         26
```

```
<210> SEQ ID NO 8
<211> LENGTH: 26
<212> TYPE: DNA
<213> ORGANISM: Artificial Sequence
<220> FEATURE:
<223> OTHER INFORMATION: Chemically synthesized

<400> SEQUENCE: 8
cgtatcgatc cgaggggggt gtatct                                              26

<210> SEQ ID NO 9
<211> LENGTH: 21
<212> TYPE: DNA
<213> ORGANISM: Artificial Sequence
<220> FEATURE:
<223> OTHER INFORMATION: Chemically synthesized

<400> SEQUENCE: 9
tcacgatgga agtcagaaac c                                                   21

<210> SEQ ID NO 10
<211> LENGTH: 20
<212> TYPE: DNA
<213> ORGANISM: Artificial Sequence
<220> FEATURE:
<223> OTHER INFORMATION: Chemically synthesized

<400> SEQUENCE: 10
ccttctcgaa ggggtactca                                                     20
```